(12) United States Patent
Wilkinson et al.

(10) Patent No.: US 9,649,464 B2
(45) Date of Patent: *May 16, 2017

(54) OXYGEN CONCENTRATOR APPARATUS AND METHOD HAVING AN ULTRASONIC DETECTOR

(75) Inventors: William R. Wilkinson, Lakeway, TX (US); Allan Sten Westersten, Georgetown, TX (US); H. David Shockley, Jr., Austin, TX (US)

(73) Assignee: Inova Labs, Inc., Austin, TX (US)

( * ) Notice: Subject to any disclaimer, the term of this patent is extended or adjusted under 35 U.S.C. 154(b) by 304 days.

This patent is subject to a terminal disclaimer.

(21) Appl. No.: 12/868,354

(22) Filed: Aug. 25, 2010

(65) Prior Publication Data

US 2011/0030689 A1 Feb. 10, 2011

Related U.S. Application Data

(63) Continuation of application No. 12/163,549, filed on Jun. 27, 2008.

(Continued)

(51) Int. Cl.
*A61M 16/00* (2006.01)
*A61M 16/10* (2006.01)
(Continued)

(52) U.S. Cl.
CPC ...... *A61M 16/101* (2014.02); *A61M 16/0003* (2014.02); *A61M 16/0051* (2013.01); *A61M 16/0069* (2014.02); *A61M 16/0672* (2014.02); *A61M 16/0677* (2014.02); *A61M 16/10* (2013.01); *A61M 16/1055* (2013.01); *A61M 16/208* (2013.01); *A61M 16/0666* (2013.01);
(Continued)

(58) Field of Classification Search
CPC .. A61M 2205/3375; A61M 2016/1025; B01D 53/047
USPC ............ 128/200.24, 204.18, 205.11, 205.12, 128/205.27, 204.22
See application file for complete search history.

(56) References Cited

U.S. PATENT DOCUMENTS 3,768,468 A 10/1973 Cox
4,194,890 A 3/1980 McCombs et al.
(Continued)

FOREIGN PATENT DOCUMENTS

EP 0978477 2/2000
EP 1205231 5/2002
(Continued)

OTHER PUBLICATIONS

European Search Report for EP08798386.
(Continued)

*Primary Examiner* — Bradley Philips
(74) *Attorney, Agent, or Firm* — Meyertons, Hood, Kivlin, Kowert & Goetzel, P.C.

(57) ABSTRACT

An oxygen concentrator may rely on a pressure swing adsorption process to produce an oxygen enriched gas stream from canisters filled with granules capable of separation of oxygen from an air stream. The adsorption process uses a cyclical pressurization and venting of the canisters to generate an oxygen enriched gas stream. Coupling an oxygen concentration sensor to the generated oxygen enriched gas stream may allow monitoring of the purity of the produced gas.

15 Claims, 31 Drawing Sheets

Related U.S. Application Data

(60) Provisional application No. 60/970,371, filed on Sep. 6, 2007.

(51) Int. Cl.
    *A61M 16/20*     (2006.01)
    *A61M 16/06*     (2006.01)
    *B01D 53/04*     (2006.01)

(52) U.S. Cl.
    CPC ............... *A61M 2016/0015* (2013.01); *A61M 2016/0021* (2013.01); *A61M 2016/0024* (2013.01); *A61M 2016/0027* (2013.01); *A61M 2016/0039* (2013.01); *A61M 2016/1025* (2013.01); *A61M 2202/0208* (2013.01); *A61M 2202/0266* (2013.01); *A61M 2205/17* (2013.01); *A61M 2205/18* (2013.01); *A61M 2205/3327* (2013.01); *A61M 2205/3372* (2013.01); *A61M 2205/3375* (2013.01); *A61M 2205/3553* (2013.01); *A61M 2205/3592* (2013.01); *A61M 2205/42* (2013.01); *A61M 2205/502* (2013.01); *A61M 2205/52* (2013.01); *A61M 2205/581* (2013.01); *A61M 2205/583* (2013.01); *A61M 2205/7518* (2013.01); *A61M 2205/8206* (2013.01); *A61M 2205/8237* (2013.01); *A61M 2209/088* (2013.01); *B01D 53/0446* (2013.01); *B01D 53/0454* (2013.01); *B01D 2253/108* (2013.01); *B01D 2256/12* (2013.01); *B01D 2259/402* (2013.01); *B01D 2259/455* (2013.01); *B01D 2259/4533* (2013.01); *G01N 2291/02881* (2013.01)

(56) References Cited

U.S. PATENT DOCUMENTS

| | | | |
|---|---|---|---|
| 4,215,798 A | 8/1980 | Acharya | |
| 4,302,224 A | 11/1981 | McCombs et al. | |
| 4,331,455 A | 5/1982 | Sato | |
| 4,342,573 A | 8/1982 | McCombs et al. | |
| 4,349,357 A | 9/1982 | Russell | |
| 4,491,459 A | 1/1985 | Pinkerton | |
| 4,519,387 A | 5/1985 | Durkan et al. | |
| 4,550,276 A | 10/1985 | Callahan et al. | |
| 4,576,616 A | 3/1986 | Mottram et al. | |
| 4,612,928 A | 9/1986 | Tiep et al. | |
| 4,630,482 A | 12/1986 | Traina | |
| 4,681,099 A | 7/1987 | Sato et al. | |
| 4,698,075 A | 10/1987 | Dechene | |
| 4,813,979 A | 3/1989 | Miller et al. | |
| 4,857,086 A | 8/1989 | Kawai | |
| 4,859,217 A | 8/1989 | Chao | |
| 4,892,566 A | 1/1990 | Bansal et al. | |
| 4,925,464 A | 5/1990 | Rabenau et al. | |
| 4,927,434 A | 5/1990 | Cordes et al. | |
| 4,938,066 A | 7/1990 | Dorr | |
| 4,938,212 A | 7/1990 | Snook et al. | |
| 4,968,329 A | 11/1990 | Keefer | |
| 4,971,049 A | 11/1990 | Rotariu et al. | |
| 4,971,609 A | 11/1990 | Pawlos | |
| 4,973,339 A | 11/1990 | Bansal | |
| 4,986,269 A | 1/1991 | Hakkinen | |
| 5,004,485 A | 4/1991 | Hamlin et al. | |
| 5,005,571 A | 4/1991 | Dietz | |
| 5,024,219 A | 6/1991 | Dietz | |
| 5,048,515 A | 9/1991 | Sanso | |
| 5,052,400 A | 10/1991 | Dietz | |
| 5,060,506 A | 10/1991 | Douglas | |
| 5,060,507 A * | 10/1991 | Urmson ............... | G01N 29/024 340/632 |
| 5,060,514 A | 10/1991 | Aylsworth | |
| 5,069,688 A | 12/1991 | Wells | |
| 5,082,473 A | 1/1992 | Keefer | |
| 5,099,193 A | 3/1992 | Moseley et al. | |
| 5,099,837 A | 3/1992 | Russel et al. | |
| 5,108,467 A | 4/1992 | Schroter et al. | |
| 5,129,924 A | 7/1992 | Schultz | |
| 5,146,918 A | 9/1992 | Kallok et al. | |
| 5,176,721 A | 1/1993 | Hay et al. | |
| 5,223,004 A | 6/1993 | Eteve et al. | |
| 5,226,933 A | 7/1993 | Knaebel et al. | |
| 5,268,021 A | 12/1993 | Hill et al. | |
| 5,275,642 A | 1/1994 | Bassine | |
| 5,315,990 A | 5/1994 | Mondry | |
| 5,340,381 A | 8/1994 | Vorih | |
| 5,351,522 A | 10/1994 | Lura | |
| 5,378,345 A | 1/1995 | Taylor et al. | |
| 5,469,372 A | 11/1995 | McBrearty et al. | |
| 5,470,378 A | 11/1995 | Kandybin et al. | |
| 5,474,595 A | 12/1995 | McCombs | |
| 5,503,146 A | 4/1996 | Froehlich et al. | |
| 5,549,720 A | 8/1996 | Miller et al. | |
| 5,575,282 A | 11/1996 | Knoch et al. | |
| 5,578,115 A | 11/1996 | Cole | |
| 5,593,478 A | 1/1997 | Hill et al. | |
| 5,603,315 A | 2/1997 | Sasso | |
| 5,672,195 A | 9/1997 | Moreau et al. | |
| 5,682,877 A | 11/1997 | Mondry | |
| 5,690,098 A | 11/1997 | Ottestad et al. | |
| 5,697,364 A | 12/1997 | Chua et al. | |
| 5,730,778 A | 3/1998 | Hill et al. | |
| 5,733,359 A | 3/1998 | Doong et al. | |
| 5,735,268 A | 4/1998 | Chua et al. | |
| 5,746,806 A | 5/1998 | Aylsworth et al. | |
| 5,764,534 A | 6/1998 | Goetting | |
| 5,766,310 A | 6/1998 | Cramer | |
| 5,792,665 A | 8/1998 | Morrow | |
| 5,827,358 A | 10/1998 | Kulish et al. | |
| 5,839,434 A | 11/1998 | Enterline | |
| 5,858,062 A | 1/1999 | McCulloh et al. | |
| 5,858,063 A | 1/1999 | Cao et al. | |
| 5,865,174 A | 2/1999 | Kloeppel | |
| 5,890,490 A | 4/1999 | Aylsworth et al. | |
| 5,893,944 A | 4/1999 | Dong | |
| 5,906,672 A | 5/1999 | Michaels et al. | |
| 5,913,307 A | 6/1999 | Taieb et al. | |
| 5,917,135 A | 6/1999 | Michaels et al. | |
| 5,922,107 A | 7/1999 | Labasque et al. | |
| 5,928,189 A | 7/1999 | Phillips et al. | |
| 5,957,133 A | 9/1999 | Hart | |
| 5,961,694 A | 10/1999 | Monereau et al. | |
| 5,968,236 A | 10/1999 | Bassine | |
| 5,988,465 A | 11/1999 | Vitale et al. | |
| 5,997,617 A | 12/1999 | Czabala et al. | |
| 6,017,315 A | 1/2000 | Starr et al. | |
| 6,030,435 A | 2/2000 | Monereau et al. | |
| 6,065,473 A | 5/2000 | McCombs et al. | |
| 6,068,680 A | 5/2000 | Kulish et al. | |
| 6,116,080 A * | 9/2000 | Logue ............... | G01N 29/024 73/24.05 |
| 6,156,101 A | 12/2000 | Naheiri et al. | |
| 6,186,142 B1 | 2/2001 | Schmidt et al. | |
| 6,186,477 B1 | 2/2001 | McCombs et al. | |
| 6,192,883 B1 | 2/2001 | Miller | |
| 6,220,244 B1 | 4/2001 | McLaughlin | |
| 6,238,458 B1 | 5/2001 | Monereau | |
| 6,253,767 B1 | 7/2001 | Mantz | |
| 6,302,107 B1 | 10/2001 | Richey et al. | |
| 6,314,957 B1 | 11/2001 | Boissin et al. | |
| 6,342,040 B1 | 1/2002 | Starr et al. | |
| 6,346,139 B1 | 2/2002 | Czabala | |
| 6,371,114 B1 | 4/2002 | Schmidt et al. | |
| 6,371,117 B1 | 4/2002 | Lindqvist et al. | |
| 6,382,931 B1 | 5/2002 | Czabala et al. | |
| 6,394,089 B1 | 5/2002 | Cantrill et al. | |
| 6,395,065 B1 | 5/2002 | Murdoch et al. | |
| 6,418,782 B1 | 7/2002 | Sato et al. | |
| 6,427,690 B1 | 8/2002 | McCombs et al. | |
| 6,446,630 B1 | 9/2002 | Todd, Jr. | |
| 6,460,402 B1 * | 10/2002 | Gomm ............... | G01F 1/667 73/24.01 |
| 6,478,850 B1 | 11/2002 | Warren | |

(56) References Cited

U.S. PATENT DOCUMENTS

| | | |
|---|---|---|
| 6,478,857 B2 | 11/2002 | Czabala |
| 6,484,721 B1 | 11/2002 | Bliss |
| 6,506,234 B1 | 1/2003 | Ackley et al. |
| 6,511,526 B2 | 1/2003 | Jagger et al. |
| 6,514,318 B2 | 2/2003 | Keefer |
| 6,520,176 B1 | 2/2003 | Dubois et al. |
| 6,527,830 B1 | 3/2003 | Neu et al. |
| 6,532,958 B1 | 3/2003 | Buan et al. |
| 6,536,431 B1 | 3/2003 | Simler |
| 6,547,851 B2 | 4/2003 | Warren |
| 6,551,384 B1 | 4/2003 | Ackley et al. |
| 6,558,451 B2 | 5/2003 | McCombs et al. |
| 6,561,187 B2 | 5/2003 | Schmidt et al. |
| 6,605,136 B1 | 8/2003 | Graham et al. |
| 6,629,525 B2 | 10/2003 | Hill et al. |
| 6,651,658 B1 | 11/2003 | Hill et al. |
| 6,655,383 B1 | 12/2003 | Lundberg |
| 6,669,758 B1 | 12/2003 | Hart et al. |
| 6,691,702 B2 | 2/2004 | Appel et al. |
| 6,694,973 B1 | 2/2004 | Dunhao et al. |
| 6,698,423 B1 | 3/2004 | Honkonen et al. |
| 6,699,307 B1 | 3/2004 | Lomax |
| 6,702,880 B2 | 3/2004 | Roberts et al. |
| 6,712,876 B2 | 3/2004 | Cao et al. |
| 6,712,877 B2 | 3/2004 | Cao et al. |
| 6,749,405 B2 | 6/2004 | Bassine |
| 6,755,895 B2 | 6/2004 | Lomax et al. |
| 6,764,534 B2 | 7/2004 | McCombs et al. |
| 6,790,260 B2 | 9/2004 | Ackley et al. |
| 6,802,889 B2 | 10/2004 | Graham et al. |
| 6,824,590 B2 | 11/2004 | Dee et al. |
| 6,827,760 B2 | 12/2004 | Kutt et al. |
| 6,837,244 B2 | 1/2005 | Yagi et al. |
| 6,866,041 B2 | 3/2005 | Hardy et al. |
| 6,866,950 B2 | 3/2005 | Connor et al. |
| 6,896,721 B1 | 5/2005 | Lynn |
| 6,908,503 B2 | 6/2005 | McCombs et al. |
| 6,918,953 B2 | 7/2005 | Lomax et al. |
| 6,929,683 B2 | 8/2005 | Lomax et al. |
| 6,935,460 B2 | 8/2005 | McCombs et al. |
| 6,938,619 B1 | 9/2005 | Hickle |
| 6,949,133 B2 | 9/2005 | McCombs et al. |
| 6,981,502 B2 | 1/2006 | McCormick et al. |
| 6,990,975 B1 | 1/2006 | Jones et al. |
| 7,000,612 B2 | 2/2006 | Jafari et al. |
| 7,007,694 B2 | 3/2006 | Aylsworth et al. |
| 7,011,092 B2 | 3/2006 | McCombs et al. |
| 7,013,898 B2 | 3/2006 | Rashad et al. |
| 7,037,358 B2 | 5/2006 | Babicki et al. |
| 7,059,323 B2 | 6/2006 | Kullik et al. |
| 7,066,985 B2 | 6/2006 | Deane et al. |
| 7,077,133 B2 | 7/2006 | Yagi et al. |
| 7,105,038 B2 | 9/2006 | Lee et al. |
| 7,114,932 B1 | 10/2006 | Bassine |
| 7,121,276 B2 | 10/2006 | Jagger et al. |
| 7,122,073 B1 | 10/2006 | Notaro et al. |
| 7,135,059 B2 | 11/2006 | Deane et al. |
| 7,156,903 B2 | 1/2007 | McCombs |
| 7,171,963 B2 | 2/2007 | Jagger et al. |
| 7,178,563 B2 | 2/2007 | Richey et al. |
| 7,179,326 B2 | 2/2007 | Nakamura et al. |
| 7,204,249 B1 | 4/2007 | Richey et al. |
| 7,213,468 B2 | 5/2007 | Fujimoto |
| 7,222,624 B2 | 5/2007 | Rashad et al. |
| 7,225,809 B1 | 6/2007 | Bowen et al. |
| 7,279,029 B2 | 10/2007 | Occhialini et al. |
| 7,306,657 B2 | 12/2007 | Yagi et al. |
| 7,329,304 B2 | 2/2008 | Bliss et al. |
| 7,329,354 B2 | 2/2008 | Mullee |
| 7,396,390 B2 | 7/2008 | Hayashi et al. |
| 7,402,193 B2 | 7/2008 | Bliss et al. |
| 7,431,032 B2 | 10/2008 | Jagger et al. |
| 7,438,745 B2 | 10/2008 | Deane et al. |
| 7,473,299 B2 | 1/2009 | Occhialini et al. |
| 7,565,907 B2 | 7/2009 | Curti et al. |
| 7,582,138 B2 | 9/2009 | Lessi et al. |
| 7,585,351 B2 | 9/2009 | Deane et al. |
| 7,604,004 B2 | 10/2009 | Jagger et al. |
| 7,604,005 B2 | 10/2009 | Jagger et al. |
| 7,686,870 B1 | 3/2010 | Deane et al. |
| 7,708,802 B1 | 5/2010 | Deane et al. |
| 7,730,887 B2 | 6/2010 | Deane et al. |
| 7,753,996 B1 | 7/2010 | Deane et al. |
| 7,757,693 B2 | 7/2010 | Toussaint |
| 7,766,010 B2 | 8/2010 | Jagger et al. |
| 7,780,768 B2 | 8/2010 | Taylor et al. |
| 7,814,906 B2 | 10/2010 | Moretti |
| 7,837,761 B2 | 11/2010 | Bliss et al. |
| 7,841,343 B2 | 11/2010 | Deane et al. |
| 7,857,894 B2 | 12/2010 | Taylor et al. |
| 7,866,315 B2 | 1/2011 | Jagger et al. |
| 7,922,789 B1 | 4/2011 | Deane et al. |
| 8,016,918 B2 | 9/2011 | LaBuda et al. |
| 8,020,558 B2 | 9/2011 | Christopher et al. |
| 8,142,544 B2 | 3/2012 | Taylor et al. |
| 8,147,597 B2 | 4/2012 | Dolensky et al. |
| 2002/0062681 A1* | 5/2002 | Livingston ............ 73/24.01 |
| 2003/0006024 A1 | 1/2003 | Wang |
| 2003/0111081 A1 | 6/2003 | Gupta |
| 2003/0140924 A1 | 7/2003 | Aylsworth et al. |
| 2004/0050255 A1 | 3/2004 | Simonds |
| 2004/0074496 A1 | 4/2004 | Hayashi et al. |
| 2004/0141874 A1 | 7/2004 | Mullinax |
| 2004/0159323 A1 | 8/2004 | Schmidt et al. |
| 2004/0182394 A1 | 9/2004 | Alvey et al. |
| 2005/0066976 A1 | 3/2005 | Wondka |
| 2005/0103341 A1* | 5/2005 | Deane et al. ......... 128/204.26 |
| 2005/0103343 A1 | 5/2005 | Gosweiler |
| 2005/0121033 A1 | 6/2005 | Starr et al. |
| 2005/0160905 A1 | 7/2005 | Whitley et al. |
| 2005/0192538 A1* | 9/2005 | Voege et al. ............ 604/167.03 |
| 2005/0217674 A1 | 10/2005 | Burton et al. |
| 2006/0084877 A1 | 4/2006 | Ujhazy et al. |
| 2006/0102181 A1 | 5/2006 | McCombs et al. |
| 2006/0112962 A1 | 6/2006 | Tebbutt et al. |
| 2006/0117957 A1 | 6/2006 | McCombs |
| 2006/0144240 A1 | 7/2006 | Lee et al. |
| 2006/0174871 A1 | 8/2006 | Jagger |
| 2006/0174875 A1 | 8/2006 | Jagger et al. |
| 2006/0174876 A1 | 8/2006 | Jagger et al. |
| 2006/0174877 A1 | 8/2006 | Jagger et al. |
| 2006/0174880 A1 | 8/2006 | Jagger et al. |
| 2006/0174881 A1 | 8/2006 | Jagger et al. |
| 2006/0174882 A1 | 8/2006 | Jagger et al. |
| 2006/0185668 A1 | 8/2006 | Jagger et al. |
| 2006/0207594 A1 | 9/2006 | Stenzler et al. |
| 2006/0230931 A1 | 10/2006 | Bliss et al. |
| 2006/0230939 A1 | 10/2006 | Bliss et al. |
| 2006/0266357 A1 | 11/2006 | McCombs et al. |
| 2007/0039466 A1 | 2/2007 | Nawata et al. |
| 2007/0044799 A1 | 3/2007 | Hete et al. |
| 2007/0056583 A1 | 3/2007 | Jagger et al. |
| 2007/0056584 A1 | 3/2007 | Jagger et al. |
| 2007/0137487 A1 | 6/2007 | Whitley et al. |
| 2007/0169623 A1 | 7/2007 | Lee et al. |
| 2007/0227539 A1 | 10/2007 | Schwaibold et al. |
| 2007/0283958 A1 | 12/2007 | Naghavi |
| 2008/0053441 A1 | 3/2008 | Gottlib et al. |
| 2008/0066741 A1 | 3/2008 | Lemahieu et al. |
| 2008/0078392 A1 | 4/2008 | Pelletier et al. |
| 2008/0202508 A1 | 8/2008 | McClain et al. |
| 2008/0223367 A1 | 9/2008 | Cox et al. |
| 2008/0302364 A1 | 12/2008 | Garde et al. |
| 2009/0065007 A1 | 3/2009 | Wilkinson et al. |
| 2009/0065526 A1 | 3/2009 | Sprinkle |
| 2009/0199855 A1 | 8/2009 | Davenport |
| 2009/0211438 A1 | 8/2009 | Thompson et al. |
| 2009/0241956 A1 | 10/2009 | Baker et al. |
| 2009/0306529 A1 | 12/2009 | Curti et al. |
| 2010/0071698 A1 | 3/2010 | Kiritake |
| 2010/0313898 A1 | 12/2010 | Richard et al. |
| 2011/0030684 A1 | 2/2011 | Wilkinson et al. |
| 2011/0030685 A1 | 2/2011 | Wilkinson et al. |
| 2011/0030686 A1 | 2/2011 | Wilkinson et al. |

(56) References Cited

U.S. PATENT DOCUMENTS

| | | |
|---|---|---|
| 2011/0030687 A1 | 2/2011 | Wilkinson et al. |
| 2011/0186054 A1 | 8/2011 | Boyd |
| 2011/0232483 A1 | 9/2011 | Haberland et al. |
| 2011/0315140 A1 | 12/2011 | Shuman |
| 2012/0055340 A1 | 3/2012 | Wilkinson et al. |
| 2012/0055474 A1 | 3/2012 | Wilkinson et al. |
| 2012/0055475 A1 | 3/2012 | Wilkinson et al. |
| 2012/0055477 A1 | 3/2012 | Wilkinson et al. |
| 2012/0055478 A1 | 3/2012 | Wilkinson et al. |
| 2012/0055480 A1 | 3/2012 | Wilkinson et al. |
| 2012/0055482 A1 | 3/2012 | Wilkinson et al. |
| 2012/0055483 A1 | 3/2012 | Wilkinson et al. |
| 2014/0137737 A1 | 5/2014 | Wilkinson et al. |
| 2014/0137744 A1 | 5/2014 | Wilkinson et al. |
| 2014/0137859 A1 | 5/2014 | Wilkinson et al. |
| 2015/0059742 A1 | 3/2015 | Wilkinson et al. |

FOREIGN PATENT DOCUMENTS

| | | |
|---|---|---|
| EP | 1568391 | 8/2005 |
| EP | 1661596 A2 * | 5/2006 |
| JP | H07-172804 | 7/1995 |
| JP | 2000354630 | 12/2000 |
| JP | 2002253675 | 9/2002 |
| JP | 2005087937 | 4/2005 |
| JP | 2005245825 | 9/2005 |
| JP | 2006095285 | 4/2006 |
| JP | 2007195820 | 8/2007 |
| JP | 4816590 | 11/2011 |
| KR | 10-0741307 | 7/2007 |
| WO | 99/22795 | 5/1999 |
| WO | 9943416 | 9/1999 |
| WO | 02/49742 | 6/2002 |
| WO | 2006108092 | 10/2006 |

OTHER PUBLICATIONS

International Preliminary Report on Patentability from PCTUS2008073884.
Bonnema, Lisa. "Breathing Easy with Plastic Blends"; http://www.appliancemagazine. com/editorial.php?articl=927&zibe=211&first=1; issue: Apr. 2005 APPLIANCE Magazine; downloaded on Jul. 26, 2007; 4 pages.
Freesyle; FreeStyleTM Portable Oxygen Concentrator, Patient Manual, AirSep, Revision; Jan. 27, 2006; 36 pages.
Lifestyle; Lifestyle TM Portable Oxygen Concentrator, Patient Manual, AirSep, Revision Date Dec. 2004; 40 pages.
Search Report for PCT Application No. PCT/US2008/073884 issued on Mar. 10, 2009.
Written Opinion for PCT Application No. PCT/US2008/073884 issued on Mar. 10, 2009.
Yang, Ralph T., "Gas Separation by Adsorption Processes", Imperial College Press, 1987, pp. 141-200. ;, 1987, pp. 141-200.
Hartzog, D. G. and Sircar, S., "Sensitivity of PSA Process Performance to Input Variables", Adsorption 1, 133-151 (1995). ;1, 133-151 (1995).
Keller II, George E., et al., "A New Process for Adsorption Separation of Gas Streams", ACS Symposium Series 135, 1980, pp. 275-286.
"Pressure Swing Adsorption" Douglas Morris Ruthven, Shamsuzzaman Farooq, and Kent S. Knaebel; VCH Publishers, 1994—Science.
Kopaygorodsky et al. "Scaling Analysis—A Valuable Technique in Engineering Teaching and Practice" Proceedings of the 2001 American Society for Engineering Education Annual Conference & Exposition Session 3513, 2001.
Tiep "Long-Term Home Oxygen Therapy", Clinics in Chest Medicine, Sep. 1990, vol. 11, No, 3, pp. 505-521.
Dietz "international Society for Mountain Medicine: An Altitude Tutorial" Jan. 29, 2006, pp. 1-2.
Kumar, R., et al., "A Versatile Process Simulator for Adsorptive Separations", Chemical Engineering Science, vol. 49, No. 18, pp. 3115-3125. ;, vol. 49, No. 18, pp. 3115-3125, 1994.
Search Report/Written Opinion for PCT Application No. PCT/US2011/050700 issued on May 1, 2012.
Office Action for U.S. Appl. No. 12/163,549 issued May 10, 2012.
Office Action for U.S. Appl. No. 12/876,848 issued Oct. 26, 2012.
Office Action for U.S. Appl. No. 12/876,854 issued Nov. 28, 2012.
Office Action for U.S. Appl. No. 12/876,878 issued Nov. 9, 2012.
Office Action for U.S. Appl. No. 12/876,874 issued Aug. 22, 2012.
Office Action for U.S. Appl. No. 12/876,882 issued Dec. 6, 2012.
Office Action for U.S. Appl. No. 12/876,884 issued Nov. 13, 2012.
Office Action for U.S. Appl. No. 12/876,890 issued Nov. 26, 2012.
Office Action for U.S. Appl. No. 12/876,890 issued Dec. 21, 2012.
Australian Examination Report for Australian Patent Application No. 2008296606 issued Mar. 27, 2013.
Search Report/Written Opinion for PCT Application No. PCT/US2013/064810 issued on Feb. 7, 2014.
Search Report/Written Opinion for PCT Application No. PCT/US2013/064817 issued on Jan. 10, 2014.
Search Report/Written Opinion for PCT Application No. PCT/US2013/064823 issued on Jan. 22, 2014.
Japanese Examination Report for JP Application No. 2010-524089 issued Apr. 22, 2013.
Japanese Examination Report for JP Application No. 2010-524089 issued Mar. 4, 2014.
EP Communication for EP Application No. 2197530 issued May 24, 2012.
EP Communication for EP Application No. 2197530 issued Feb. 5, 2014.
Australian Examination Report for Australian Patent Application No. 2008296606 issued Jul. 11, 2014.
Search Report for EP Application No. 2613838 issued Apr. 17, 2013.
EP Communication for EP Application No. 2613838 issued Mar. 17, 2015.
Office Action for U.S. Appl. No. 12/163,549 issued Aug. 14, 2013.
Office Action for U.S. Appl. No. 12/163,549 issued Dec. 20, 2013.
Office Action for U.S. Appl. No. 12/876,848 issued May 23, 2013.
Office Action for U.S. Appl. No. 12/876,854 issued Jul. 18, 2013.
Office Action for U.S. Appl. No. 12/876,854 issued Feb. 14, 2014.
Office Action for U.S. Appl. No. 12/876,878 issued Jun. 19, 2013.
Office Action for U.S. Appl. No. 12/876,878 issued Feb. 5, 2014.
Office Action for U.S. Appl. No. 12/876,878 issued Nov. 20, 2014.
Office Action for U.S. Appl. No. 12/876,874 issued Feb. 15, 2013.
Office Action for U.S. Appl. No. 12/876,882 issued Jul. 30, 2013.
Office Action for U.S. Appl. No. 12/876,882 issued Oct. 8, 2014.
Office Action for U.S. Appl. No. 12/876,890 issued Aug. 16, 2013.
Office Action for U.S. Appl. No. 12/876,890 issued Mar. 12, 2014.
Office Action for U.S. Appl. No. 12/876,890 issued Nov. 28, 2014.
Office Action for U.S. Appl. No. 12/876,899 issued Aug. 19, 2013.
Office Action for U.S. Appl. No. 12/876,899 issued Aug. 28, 2014.
Office Action for U.S. Appl. No. 12/876,899 issued May 5, 2015.
Office Action for U.S. Appl. No. 14/053,029 issued Sep. 24, 2014.
Office Action for U.S. Appl. No. 14/053,029 issued Mar. 12, 2015.

* cited by examiner

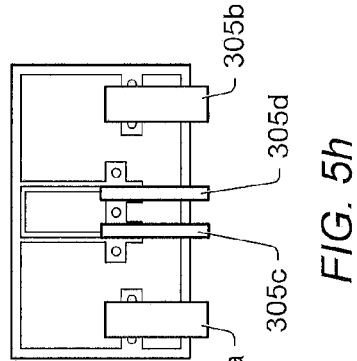
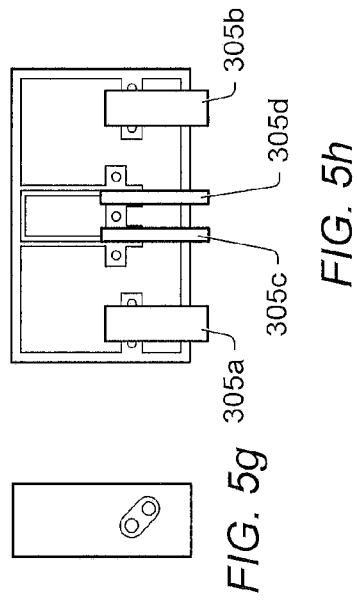
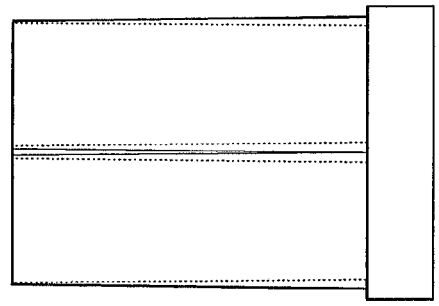
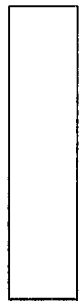
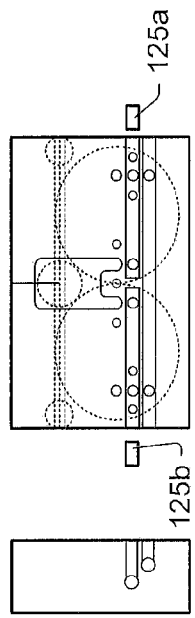
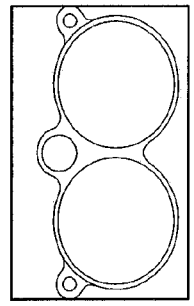
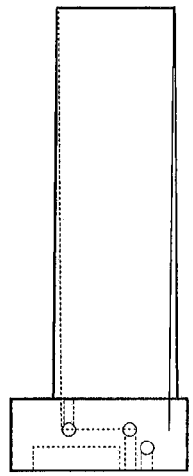
FIG. 5a
FIG. 5b
FIG. 5c
FIG. 5d
FIG. 5e
FIG. 5f
FIG. 5g
FIG. 5h

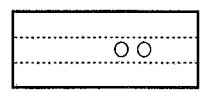
FIG. 6f
FIG. 6b
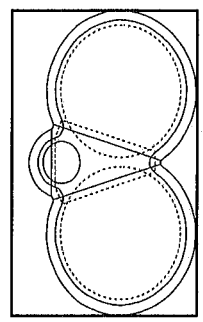
FIG. 6c
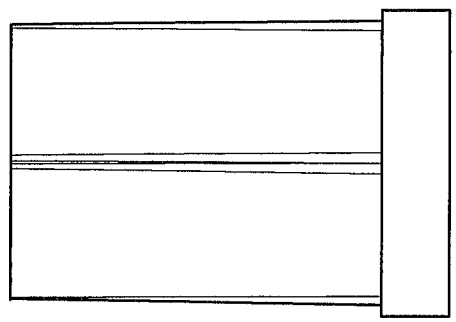
FIG. 6d
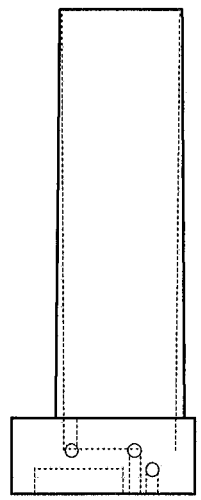
FIG. 6a
FIG. 6e

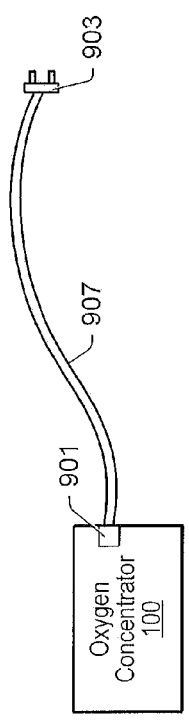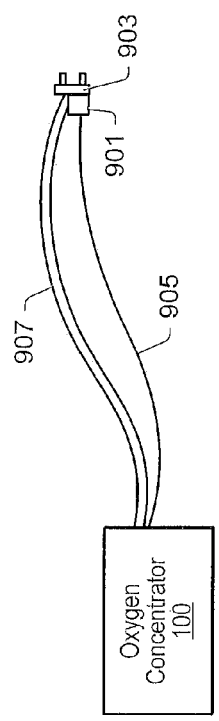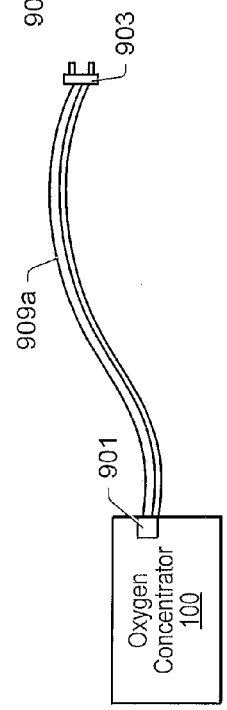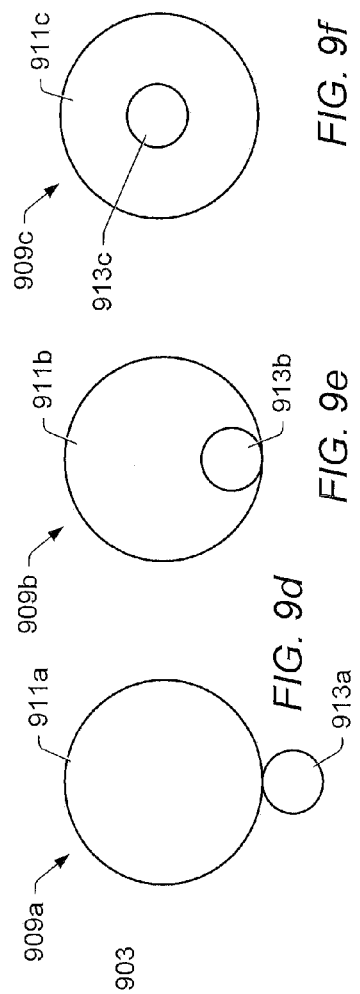

OXYGEN CONCENTRATOR APPARATUS AND METHOD HAVING AN ULTRASONIC DETECTOR

PRIORITY

This application is a Continuation of U.S. patent application Ser. No. 12/163,549 entitled "OXYGEN CONCENTRATOR APPARATUS AND METHOD", filed on Jun. 27, 2008, which claims the benefit of priority of U.S. Provisional Patent Application Ser. No. 60/970,371 titled "Oxygen Concentrator Apparatus and Method", filed on Sep. 6, 2007, both of which are hereby incorporated by reference in its entirety as though fully and completely set forth herein.

BACKGROUND

1. Field of the Invention

The present invention relates generally to health equipment and, more specifically, to oxygen concentrators.

2. Description of the Related Art

Patients (e.g., those suffering with diseases such as emphysema, congestive heart failure, acute or chronic pulmonary insufficiency, etc.) may require supplemental oxygen. Other people (e.g., obese individuals) may also require supplemental oxygen, for example, to maintain elevated activity levels. Doctors may prescribe oxygen concentrators or portable tanks of medical oxygen for these patients. Usually a specific oxygen flow rate is prescribed (e.g., 1 liter per minute (LPM), 2 LPM, 3 LPM, etc.) Oxygen concentrators used to provide these flow rates may be bulky and heavy making ordinary ambulatory activities with them difficult and impractical. Portable tanks of medical oxygen may also be heavy and contain limited amounts of oxygen.

Oxygen concentrators may take advantage of pressure swing absorption. Pressure swing absorption may involve using a compressor to increase air pressure inside a canister that contains granules of a micro-porous mineral. As the pressure increases, certain air molecules may become smaller and may be absorbed into the micro-pores of the granules. An example of such a granule is found in certain volcanic ash. Synthetic granules (e.g., zeolite) may also be available in various granule and pore sizes. These granules may thus be used to separate gases of different molecular size (e.g., zeolite may be used to separate nitrogen and oxygen). Ambient air usually includes approximately 78% nitrogen and 21% oxygen with the balance comprised of argon, carbon dioxide, water vapor and other trace elements. When pressurized air is applied to the granules, nitrogen in the air may be absorbed in the micro-pores of the granules because of the smaller size of the nitrogen molecule. As the granules are saturated, the remaining oxygen may be allowed to flow through the canister and into a holding tank. The pressure in the canister may then be vented from the canister resulting in the previously absorbed nitrogen being released from the pores in the granules. A small portion of the bled oxygen may be used to further purge the nitrogen from the canister. The process may then be repeated using additional ambient air. By alternating canisters in a two-canister system, one canister can be collecting oxygen while the other canister is being purged (resulting in a continuous separation of the oxygen from the nitrogen). In this manner, oxygen can be accumulated out of the air for a variety of uses include providing supplemental oxygen to patients.

Prior art oxygen concentrators may have several limitations. For example, the compressor on the oxygen concentrator may be operated at a level required to meet the demands of the user regardless of the breathing rate of the user. In addition, the length of the supply tubing to the nasal cannula or mask from the oxygen concentrator may be limited to 6 to 8 feet. This limitation may be a problem for users using the device in their sleep. Prior art oxygen concentrators may also include a limited sensor and alarm to notify a user if the oxygen supplied by the oxygen concentrator is too low. Currently oxygen sensors in oxygen concentrators use a heated filament as a component. In addition, time, pressure and orifice size are used to determine a volume of air delivered to a user of an oxygen concentrator (however, this measurement technique may not account for pressure fluctuations).

SUMMARY

In various embodiments, an oxygen concentrator for concentrating oxygen may include canisters (e.g., to hold zeolite) integrated into a molded body. The oxygen concentrator may be made of one or more plastic molded parts (i.e., housing components) and may further include valves, flow restrictors (e.g., press fit flow restrictors), air pathways, and other components coupled to or integrated into the one or more housing components. In some embodiments, the canisters may be injection molded (e.g., using plastic). The injection molded housing components may include air pathways for air flowing to and from the canisters. In some embodiments, valves may be coupled to the one or more housing components to direct air through the air pathways. In some embodiments, one or more compressors (e.g., a dual-pump diaphragm compressor) may compress air through the canisters. Zeolite (or another granule) in the canisters may separate nitrogen and oxygen in the air as the air is compressed through the canisters. Some of the separated oxygen may also be used to vent nitrogen from the canisters. In some embodiments, a spring baffle may be used to bias the granules in the canister to avoid damage to the granules when the oxygen concentrator is moved. The spring baffle may be a single molded part (e.g., injection molded part). In some embodiments, the oxygen concentrator may include two-step actuation valves. Two step actuation valve may be operable to be opened by application of a first voltage and further operable to be held open by a second voltage (the second voltage may be less than the first voltage to conserve energy). In some embodiments, a solar panel may be coupled to a battery of the oxygen concentrator to charge the battery using solar energy.

In some embodiments, a pressure transducer coupled to the oxygen concentrator may detect a change in pressure corresponding to a start of a user's breath. A processor coupled to the pressure transducer may execute program instructions to implement a first mode in which a sensitivity of the pressure transducer is attenuated. In a second mode, the sensitivity of the pressure transducer may not be attenuated. For example, the sensitivity of the pressure transducer may be attenuated in windy environments or while the user is active. The sensitivity may not be attenuated, for example, while the user is asleep or otherwise sedentary.

In various embodiments, the pressure transducer, coupled to the oxygen concentrator, may be used to detect a breathing rate of the user of the oxygen concentrator. The processor coupled to the pressure transducer may execute program instructions to adjust power to the one or more compressors based on the breathing rate of the user of the oxygen concentrator. In some embodiments, the compressors may switch between a first phase of operation in which only a subset of the compressors operate and a second phase of operation in which additional compressors (e.g., all available compressors) operate. For example, fewer compressors may be used during lower user breathing rates.

In some embodiments, the oxygen concentrator may use a dual lumen (including a first tube and a second tube). The first tube may be used to deliver oxygen to the user's nose and the second tube may extend to the entrance of the user's nose to communicate a change in pressure (e.g., from the start of a breath through the user's nose) from the entry of the user's nose to the oxygen concentrator. In some embodiments, the second tube may have a smaller radius than the first tube to allow for increased sensitivity to pressure changes in the second tube.

In some embodiments, a transducer may be coupled to the prongs of the nasal cannula to detect a change in pressure resulting from a start of a breath taken by the user. In some embodiments, a Hall-effect sensor may be used at the nasal cannula or at the oxygen concentrator to detect air movement (e.g., due to a user's breath). The Hall-effect sensor may use a magnet coupled to a vane (inserted into the nasal cannula) to detect movement of air in the nasal cannula.

In some embodiments, an ultrasonic sensor may be used to detect the presence of a gas (e.g., to detect the concentration of oxygen in air delivered to a user). In some embodiments, the ultrasonic sensor may be placed on a chamber of the oxygen concentrator that receives air to be delivered to the user. An ultrasonic emitter of the ultrasonic sensor may provide an ultrasonic sound wave through the chamber and an ultrasonic receiver may detect the ultrasonic sound wave that has traveled through the air of the chamber. A processor coupled to the ultrasonic emitter and the ultrasonic receiver may execute program instructions to determine a speed of the sound wave through the chamber (the speed of the sound wave may indicate a relative concentration of a constituent of the gas (e.g., the concentration of oxygen)).

In some embodiments, an audio device (e.g., an MP3 (Moving Picture Experts Group Layer-3 Audio) player, mobile phone, etc.) may be integrated into the oxygen concentrator (e.g., integrated into an outer housing of the oxygen concentrator). A microphone and headphone may be coupled to the audio device through a wire or may be wirelessly connected. In some embodiments, the microphone may be coupled to a nasal cannula or other oxygen delivery mechanism coupled to the oxygen concentrator. Other configurations are also contemplated. The headset/microphone combination may also be used with the oxygen concentrator for hands-free cellular phone use. Other uses are also contemplated.

In some embodiments, various components of the oxygen concentrator may be arranged in one or more housings (e.g., a foam housing inside of a light-weight plastic enclosure). In some embodiments, the foam housing may include passages for air flow and/or electrical connections between components of the oxygen concentrator. Other configurations are also contemplated. In some embodiments, additional housings may be used.

BRIEF DESCRIPTION OF THE DRAWINGS

A better understanding of the present invention may be obtained when the following detailed description is considered in conjunction with the following drawings, in which:

FIGS. 5a-h illustrate various views of the first housing component of the oxygen concentrator, according to an embodiment.

FIGS. 6a-h illustrate additional views of the internal structure of the first housing component of the oxygen concentrator, according to an embodiment.

FIGS. 9a-f illustrate different hose/pressure transducer configurations, according to an embodiment.

Figure 1A:
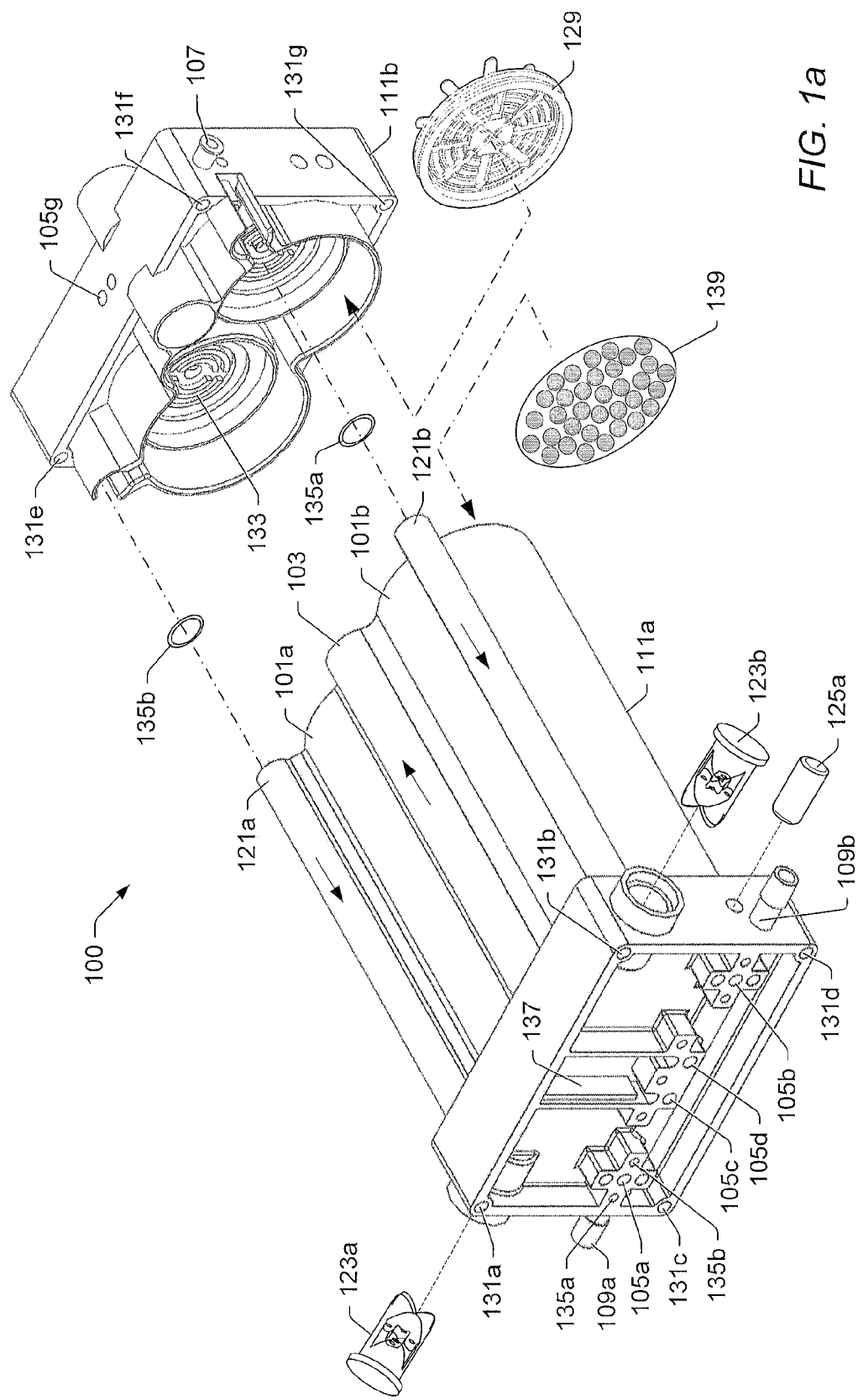
FIGS. 1a-b illustrate two molded oxygen concentrator housing components, according to an embodiment.
Figure 1B:
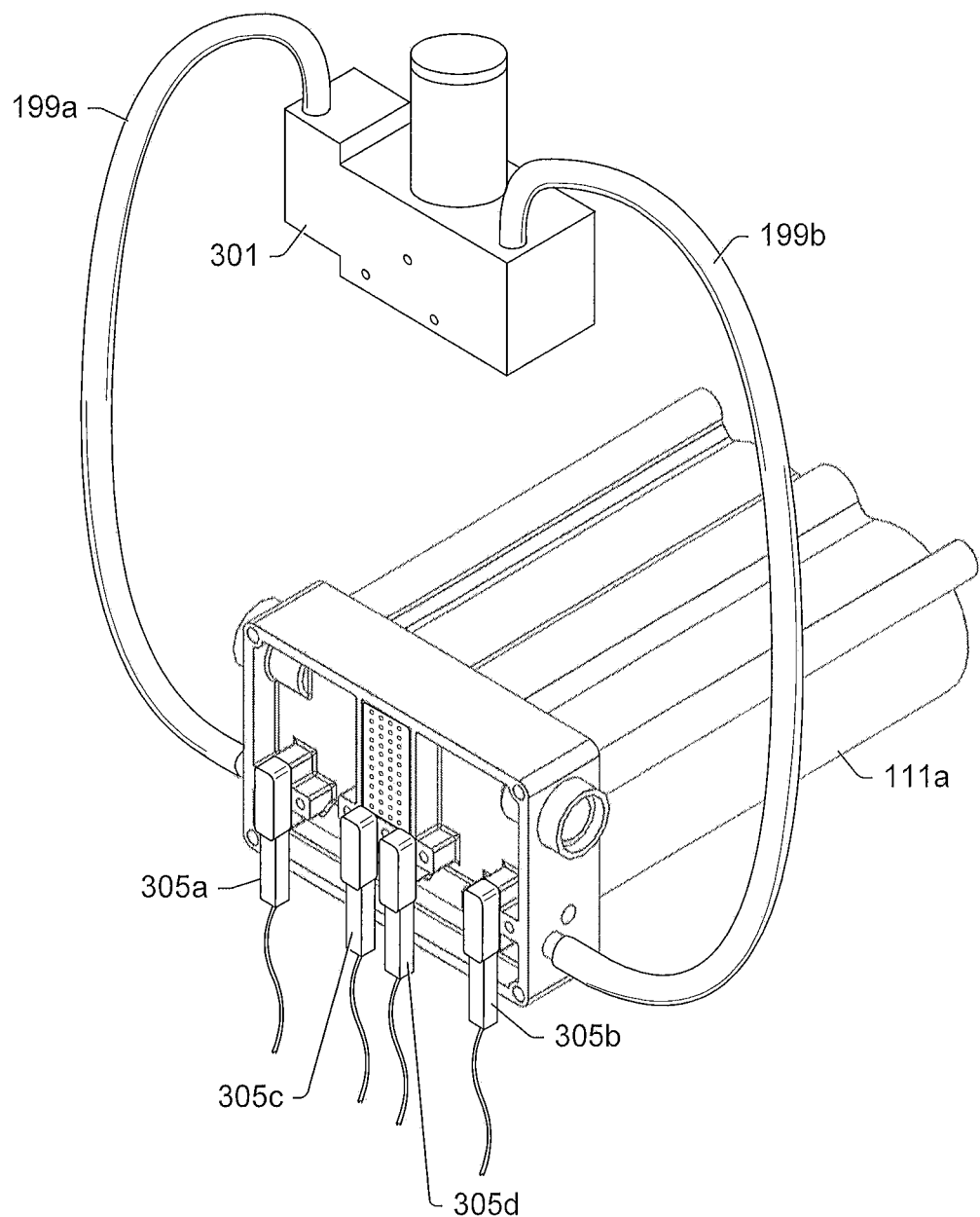
Figure 2A:
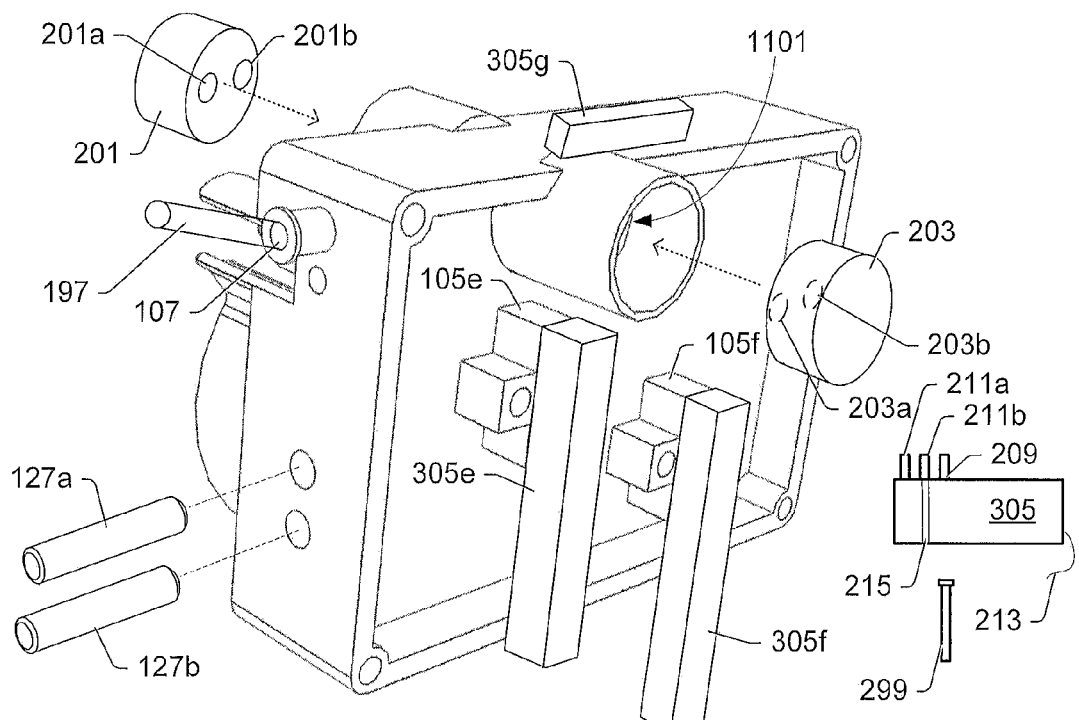
FIGS. 2a-b illustrates the second housing component of the oxygen concentrator, according to an embodiment.
Figure 2B:
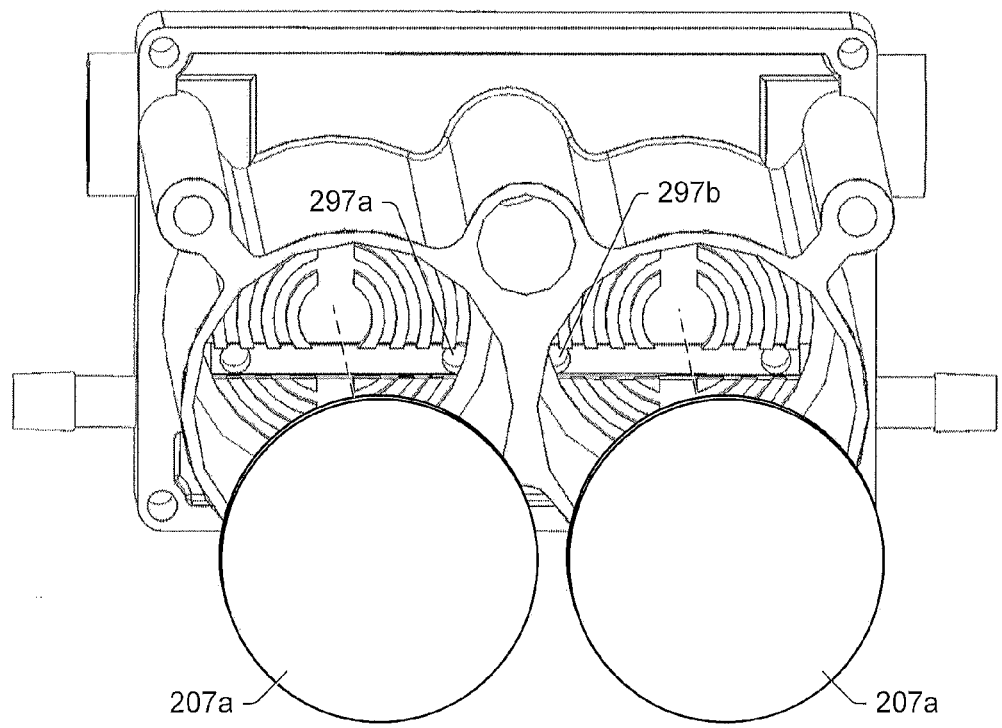

While the invention is susceptible to various modifications and alternative forms, specific embodiments thereof are shown by way of example in the drawings and will herein be described in detail. It should be understood, however, that the drawings and detailed description thereto are not intended to limit the invention to the particular form disclosed, but on the contrary, the intention is to cover all modifications, equivalents, and alternatives falling within the spirit and scope of the present invention as defined by the appended claims. Note, the headings are for organizational purposes only and are not meant to be used to limit or interpret the description or claims. Furthermore, note that the word "may" is used throughout this application in a permissive sense (i.e., having the potential to, being able to), not a mandatory sense (i.e., must). The term "include", and derivations thereof, mean "including, but not limited to". The term "coupled" means "directly or indirectly connected".

DETAILED DESCRIPTION OF THE EMBODIMENTS

Figure 3:
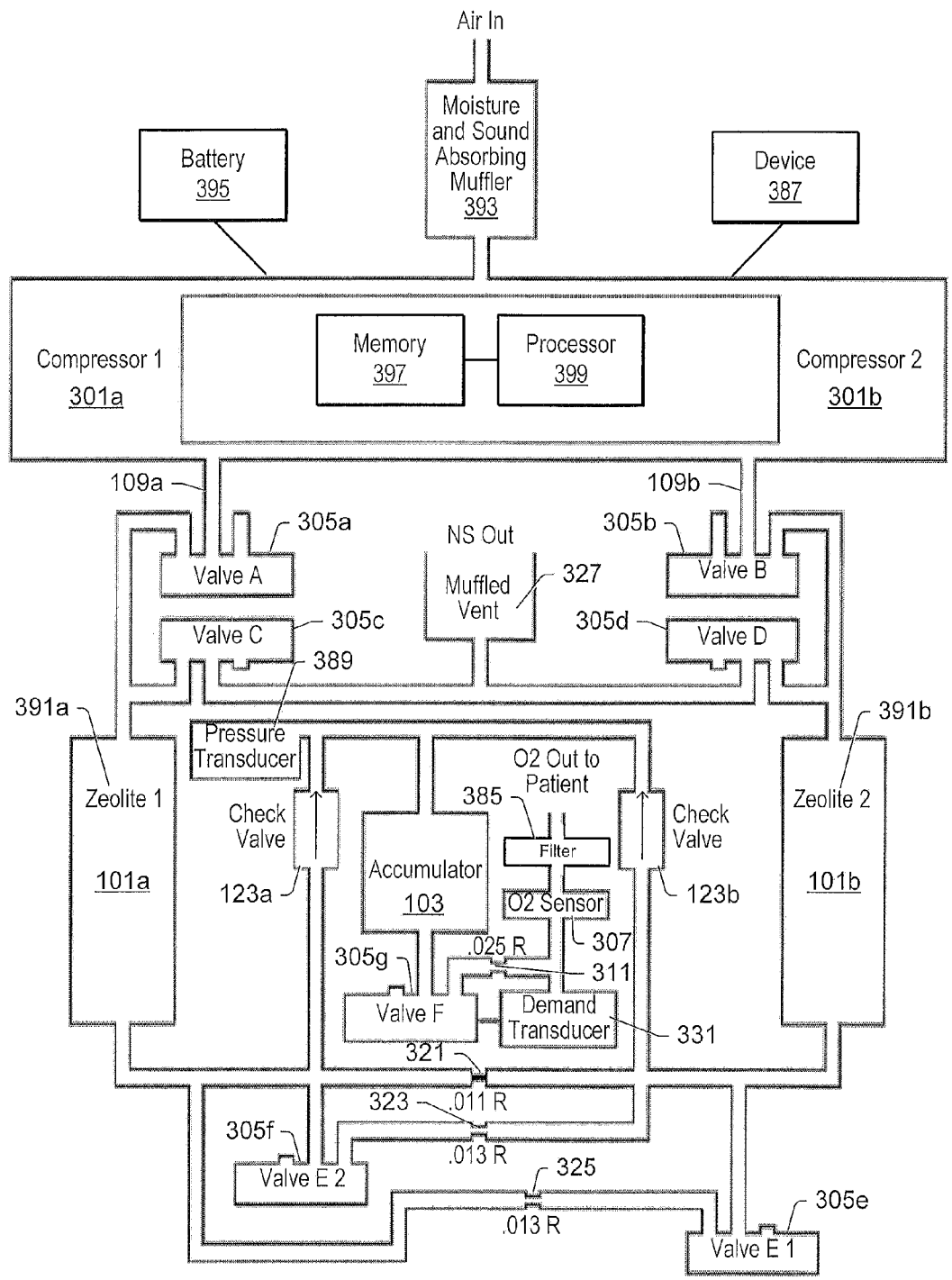
FIG. 3 illustrates a diagram of the components of the oxygen concentrator, according to an embodiment.

FIGS. 1a-2b illustrate various views of housing components 111a-b for an oxygen concentrator 100, according to an embodiment. In some embodiments, the oxygen concentrator 100 may concentrate oxygen out of the air to provide supplemental oxygen to a user. The oxygen may be collected from ambient air by pressurizing the ambient air in a canister (e.g., canisters 101a-b) with granules 139 (e.g., molecular sieve granules) such as zeolite 391 (see FIG. 3). Other materials (used instead of or in addition to zeolite 391) may be used. In some embodiments, the air may be pressurized in the canister 101 using one or more compressors 301. In some embodiments, the ambient air may be pressurized in the canisters 101 to a pressure approximately in a range of 13-20 pounds per square inch (psi). Other pressures may also be used (e.g., if a different granule type is used). Under pressure, the nitrogen molecules in the pressurized ambient air may enter the pores of the granules 139 in the canister 101 which may hold the nitrogen molecules as oxygen molecules flow through the canister 101 and out of a respective exit aperture 601 (see FIG. 6). While examples provided herein describe separating nitrogen and oxygen, it is to be understood that other embodiments may include separating other atom/molecules types. In some embodiments, the oxygen molecules leaving aperture 601 may be collected in an oxygen accumulator 103 prior to being provided to a user through outlet 107. In some embodiments, a tube (e.g., tube 907 in FIGS. 9a-b) may be coupled to the outlet 107 to deliver the oxygen to the user through a nasal cannula 903. In some embodiments, tube 907 may be coupled to an exit nozzle 2111a,b (see FIGS. 21a-b) that is coupled to outlet 107 through a silicone rubber tube 197 (other materials for the tube 197 are also contemplated). Other delivery mechanisms and routes are also contemplated. For example, the outlet may include a tube that directs the oxygen toward a user's nose and/or mouth that may not be directly coupled to the user's nose. In some embodiments, the oxygen provided to the user may be of 90 percent or greater purity (e.g., 97 percent purity). Other oxygen concentrations are also contemplated (e.g., lower purity levels may be desired).

In some embodiments, after applying the initial pressurized air to a canister 101 (e.g., canister 101a), the pressure in the canister 101 may be released, and the nitrogen molecules in the canister 101 may be expelled from the oxygen concentrator 100 (e.g., through respective valve 305c or 305d and then through muffled vent 327). Other exit mechanisms may also be used. In some embodiments, the canister 101 may be further purged of nitrogen using concentrated oxygen that is introduced into the canister 101 through respective aperture 601 (e.g., from oxygen being concentrated from the other canister 101). In some embodiments, the oxygen concentrator 100 may include two or more canisters 101. For example, while canister 101a is being purged of nitrogen, canister 101b may be collecting oxygen. Other configurations are also contemplated (e.g., one canister, four canisters, etc.).

In some embodiments, pressurized air from the compressors 301 may enter air inlets 109a-b and then may be directed using various valves 305 (attached to valve seats 105) and internal air pathways. As shown in FIGS. 1a-3, valve seats 105a-g may correspond to respective valves 305a-g (e.g., valve 305a is seated in valve seat 105a, etc.). As seen in the example valve 305 in FIG. 2a, valves 305 may include high pressure stems (e.g., stem 211a) and low pressure stems (e.g., stem 211b). The valves 305 may also include gaskets around the stems (e.g., gasket 209). The valves 305 may be actuated/powered through electrical connection 213. In some embodiments, the valves 305 may be coupled to and controlled by processor 399. The valves 305 may be coupled to their respective valve seats 105 (e.g., through size 256 screws 299 through slots 215 on either side of the valve 305 and into their respective fastening apertures (e.g., screw apertures 135a,b)). The valves 305 may also be coupled to the valve seats 105 through other techniques (e.g., using adhesive, rivets, etc.). Other valve and valve seat configurations are also contemplated.

In some embodiments, air may be pulled into the oxygen concentrator 100 through compressors 301a-b (which may be dual-pump diaphragm compressors). In some embodiments, air may flow into the air inlets 109a-b from compressors 301a-b (e.g., one inlet per respective compressor). In some embodiments, one of valves 305a or 305b may be closed (e.g., as signaled by processor 399) resulting in the combined output of both compressors 301 flowing through the other respective valve seat 105/valve 305 into a respective canister 101 (e.g., either canister 101a or canister 101b). For example, if valve 305b (seated in valve seat 105b) is closed, the air from both compressors 301 may flow through valve 305a (seated in valve seat 105a). If valve 305a is closed, the air from both compressors 301 may flow through valve 305b. In some embodiments, valve 305a and valve 305b may alternate to alternately direct the air from the compressors 301 into respective canisters 101a or 101b. In some embodiments, if one of the two compressors 301 fails, the working compressor's output may be alternately directed between canisters 101a,b. This may allow the oxygen concentrator 100 to at least partially work (e.g., on half output) until the user can arrange another oxygen source.

Figures 6G, 6H:
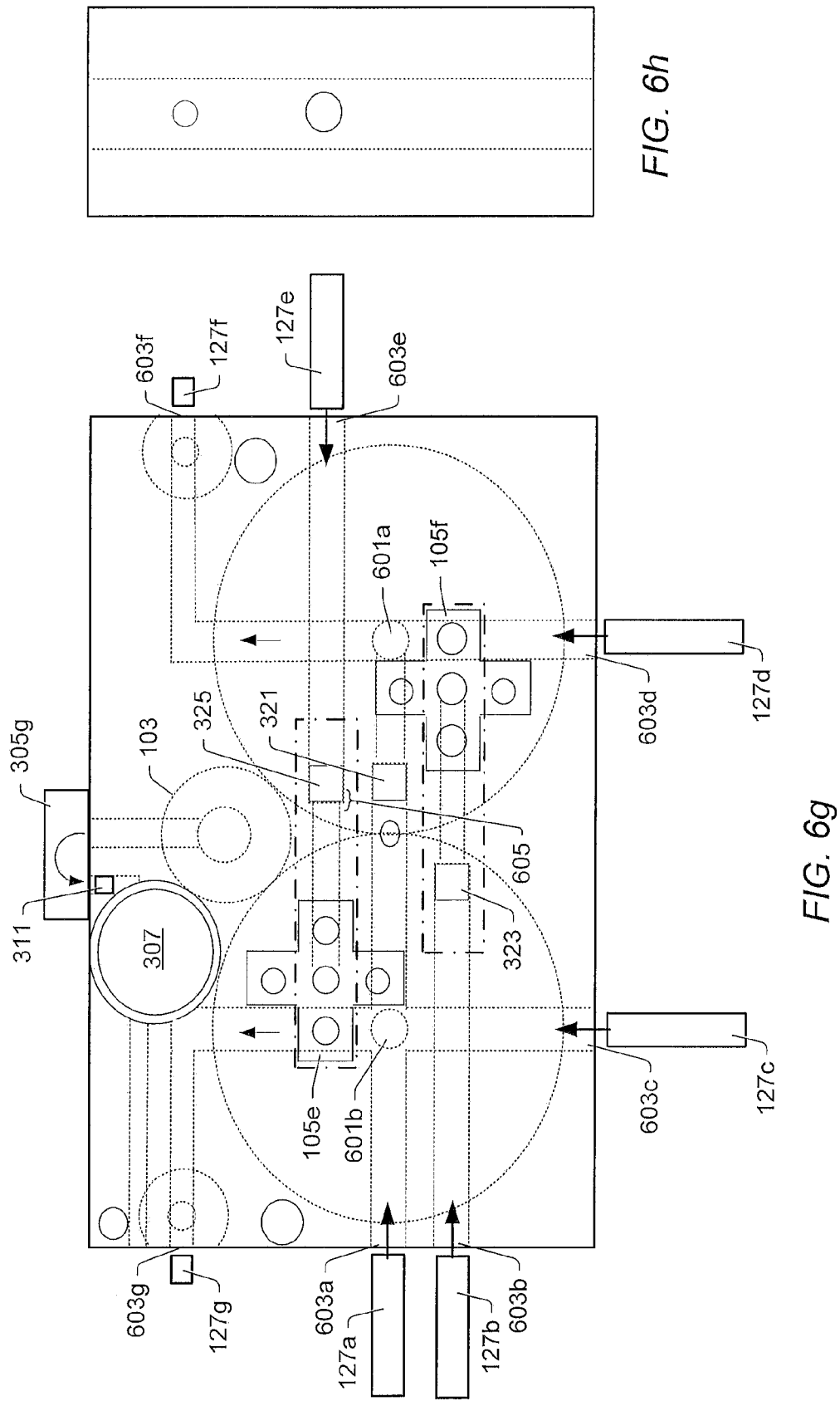

In some embodiments, as air flows through respective canister 101a or 101b, oxygen may pass through the granules 139 in the canister 101 while the nitrogen is retained in the granules 139. As seen in FIG. 6G, the oxygen may pass through opening 601a at the end of canister 101a, through side tube 121a, through check valve 123a, and into oxygen accumulator 103. Alternately, the oxygen may pass through opening 601b at the end of canister 101b, through side tube 121b, through check valve 123b, and into oxygen accumulator 103. From oxygen accumulator 103, the air may flow through valve 305g (which may be a high pressure F-valve) seated in valve seat 105g. In some embodiments, the air may flow through a flow restrictor 311 (e.g., a 0.025 R flow restrictor). Other flow restrictor types and sizes are also contemplated. In some embodiments, a separate restrictor may not be used (e.g., the diameter of the air pathway in the housing may be restricted). The air may then flow through an oxygen sensor (e.g., ultrasonic sensor 307 comprised of an ultrasonic emitter 201 and receiver 203), a filter 385 (e.g., to filter bacteria, dust, granule particles, etc), through silicone rubber tube 197, and then out of the oxygen concentrator 100 and to the user (e.g., through a tube 907 and nasal cannula 903 coupled to outlet 107).

Figure 11:
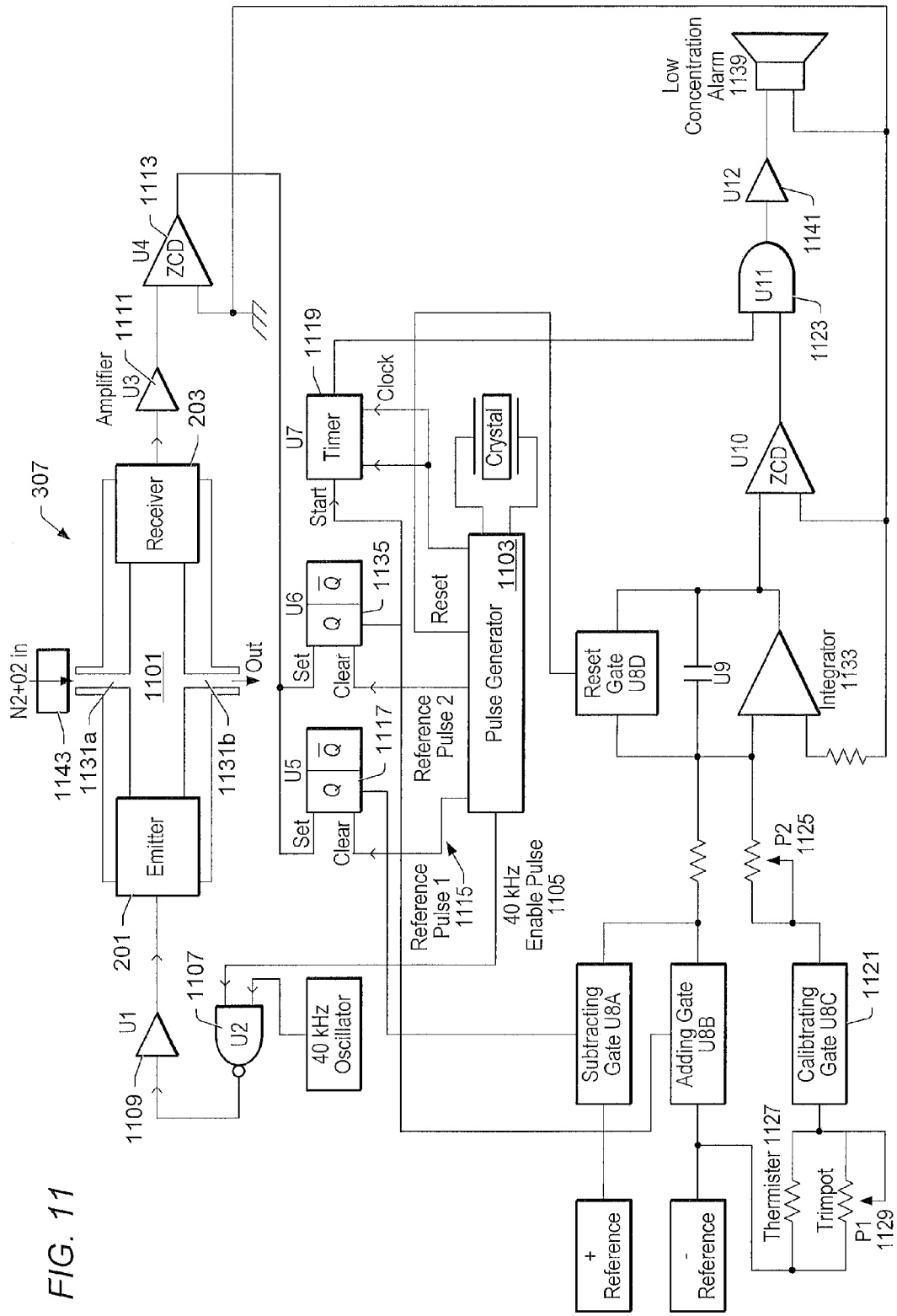
FIG. 11 illustrates a circuit diagram of an ultrasonic sensor assembly, according to an embodiment.

In some embodiments, ultrasonic emitter 201 may include multiple ultrasonic emitters (e.g., emitters 201a,b) and ultrasonic receiver 203 may include multiple ultrasonic receivers (e.g., receivers 203a,b). In some embodiments, the multiple ultrasonic emitters and multiple ultrasonic receivers may be axially aligned (e.g., across the gas mixture flow path which may be perpendicular to the axial alignment). Other emitter/receiver configurations are also contemplated. In some embodiments, the ultrasonic sensor 307 and, for example, a gas flow meter 1143 (as seen in FIG. 11) may provide a measurement of flow delivery (or actual amount of oxygen being delivered). For example, the gas flow meter 1143 may use the Doppler effect to measure a volume of gas provided and the ultrasonic sensor 307 may provide the concentration of oxygen of the gas provided. These two measurements together may be used by the processor to determine an approximation of the actual amount of oxygen provided to the user. Other sensors may also be used in flow delivery measurement.

In some embodiments, valve 305a may be closed and valve 305c (seated in valve seat 105c) may be opened to direct nitrogen (under pressure) out of canister 101a and through the muffled vent out 327. Similarly, valve 305b may be closed and valve 305d (seated in valve seat 105d) may be opened to direct nitrogen (under pressure) out of canister 101b and through the muffled vent out 327.

In some embodiments, a portion of the collected oxygen may be transferred from one canister 101 (e.g., the canister 101 currently producing oxygen) to the back of the other canister 101 (e.g., the canister 101 currently venting nitrogen) in order to further purge the nitrogen. The oxygen may travel through flow restrictors 321, 323, and 325 between the two canisters 101. Flow restrictor 321 may be a trickle flow restrictor. Flow restrictor 321 may be a 0.011 R flow restrictor (e.g., with a radius 0.011*the radius of the tube it is inside) and flow restrictor 323 and flow restrictor 325 may be a 0.013 R flow restrictors. Other flow restrictor types and sizes are also contemplated. For example, flow restrictor 321 may be a 0.009 R flow restrictor. In some embodiments, the flow restrictors may be press fit flow restrictors that restrict air flow by introducing a narrower radius in their respective tube. In some embodiments, the press fit flow restrictors may be made of sapphire, metal or plastic (other materials are also contemplated).

Valve 305e and valve 305f may be opened to direct oxygen from the producing canister 101 to the venting canister 101. The valves may be opened for a short duration during the venting process (and may be closed otherwise) to prevent excessive oxygen loss out of the purging canister 101. Other durations are also contemplated. The pair of equalization/vent valves 305e,f may work with flow restrictors 323 and 325 to optimize the air flow balance between the two canisters 101a,b. This may allow for better flow control for venting the canisters 101a,b with oxygen from the other of canisters 101a,b. It may also provide better flow direction between the two canisters 101a,b. For example, when directing oxygen from canister 101b to canister 101a to vent the nitrogen out of canister 101a, oxygen may flow through flow restrictor 323 and then open valve 305f on a first air pathway, and through open valve 305e and then flow restrictor 325 on the second air pathway (one air pathway ideal and one air pathway less ideal). Similarly, when directing oxygen from canister 101a to canister 101b to vent the nitrogen out of canister 101b, oxygen may flow through open valve 305f and then flow restrictor 323 on one air pathway and through flow restrictor 325 then open valve 305e on the second air pathway (one air pathway ideal and one air pathway less ideal). Therefore, a similar volume of oxygen may be used from each canister 101 when purging the other canister 101. The opposite arrangement of the valve and flow restrictor on parallel air pathways may equalize the flow pattern of the oxygen between the two canisters 101. If not equalized, more oxygen may be used in venting one of the canisters 101 than the other of the canisters 101 (resulting in less oxygen available to the user on every other cycle). Equalizing the flow may allow for a steady amount of oxygen available to the user over multiple cycles and also may allow a predictable volume of oxygen to purge the other of the canisters 101. Other numbers of valves and/or flow resistors are also contemplated. Other arrangements are also contemplated. For example, one air pathway may be provided with a balanced flow pattern in either direction. In some embodiments, the air pathway may include a first flow restrictor, a valve, and a second flow restrictor (of similar size as the first flow restrictor) such that when the valve is open, air flows through the restrictors and valve in a similar pattern (restrictor, valve, restrictor) regardless of direction. In some embodiments, the air pathway may not have restrictors but may instead have a valve with a built in resistance (or the air pathway itself may have a narrow radius to provide resistance) such that air flow through the valve has the same resistance regardless of direction through the valve.

Figure 4:
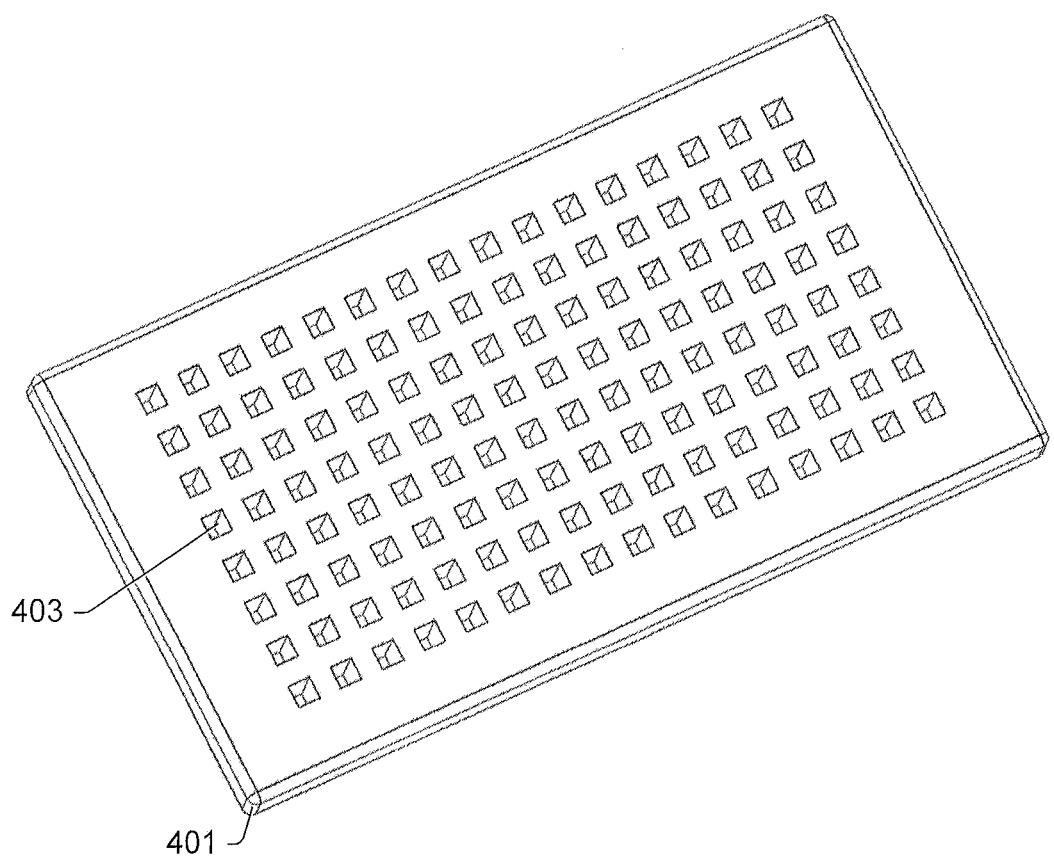
FIG. 4 illustrates a vented lid for the oxygen concentrator, according to an embodiment.

Air being vented out of the canisters 101 may travel through canister exit aperture 297a or 297b, through respective valve 305c or 305d, through the muffled vent out 137, and then through the vent 401 (e.g., see FIG. 4). The muffled vent out 137 may include open cell foam (or another material) between the nitrogen exit aperture 217a of the housing component 111a and the vent 401 to muffle the air leaving the oxygen concentrator 100. Other muffling techniques are also contemplated. In some embodiments, the combined muffling components/techniques may provide for oxygen concentrator operation at a sound level below 50 decibels. The oxygen concentrator may also operate at lower or higher sound levels. In some embodiments, the vent 401 may include apertures 403 that may be smaller in cross section than the open cell foam in the muffled vent out 137. This may allow air to exit while keeping the open cell foam in the muffled vent out 137. In some embodiments, the vent 401 may be made of a molded plastic (e.g., injection molded). Other materials are also contemplated. In some embodiments, the vent 401 may be coupled to the muffled vent out 137 of housing component 111a through an adhesive or solvent weld. Other coupling techniques are also contemplated (e.g., the vent 401 may snap in place).

In some embodiments, the valves 305 may be silicon plunger solenoid valves (other valves are also contemplated). Plunger valves may be quiet and have low slippage. In some embodiments, a two-step valve actuation voltage may be used to control the valves 305. For example, 24 volts (V) may be applied to the valve to open the valve 305, and then the voltage may be reduced to 7 V to keep the valve 305 open. In some embodiments, the voltages and the duration of the voltages may be controlled by processor 399. The valves 305 may require more voltage to overcome static friction, but once open, less voltage may be required to keep the valve 305 open (the sliding friction may be less than the static friction on the valve 305). Using less voltage to keep the valve 305 open may use less power (Power=Voltage*Current). Lower power requirements may lead to a longer battery life. In some embodiments, the voltage may be applied as a function of time that is not necessarily a stepped response (e.g., a curved downward voltage between an initial 24 V and 7 V). Other response patterns are also contemplated. Other voltages are also contemplated (e.g., voltages larger or smaller than 24V, 7V). For example, different voltages may be used for different valves.

In some embodiments, the housing for the oxygen concentrator 100 may include two housing components 111*a-b*. The housing components 111*a-b* may be formed separately and then coupled together (other numbers of housing components are also contemplated). In some embodiments, the housing components 111*a-b* may be injection molded (e.g., from an injection die molded plastic). Other manufacturing techniques are also contemplated (e.g., compression molding). The housing components 111*a-b* may be made of a thermoplastic such as polycarbonate, methylene carbide, polystyrene, acrylonitrile butadiene styrene (ABS), polypropylene, polyethylene, or polyvinyl chloride. Other materials are also contemplated (e.g., the housing components 111*a-b* may be made of a thermoset plastic or metal (such as stainless steel or a light-weight aluminum alloy)). Light-weight materials may be used to reduce the weight of the oxygen concentrator 100. In some embodiments, the two housings 111*a* and 111*b* may be fastened together using screws or bolts. For example, screws may be placed through apertures 131*a-g* (e.g., one screw through aperture 131*a* and 131*e*, etc.). Other fastening techniques are also contemplated (e.g., rivets). As another example, the housing components 111*a,b* may be solvent welded together.

As shown, valve seats 105*a-f* and air pathways may be integrated into the housing components 111*a-b* to reduce a number of seal connections needed throughout the air flow of the oxygen concentrator 100 (this may reduce leaks and potential failure points). In various embodiments, the housing components 111*a-b* of the oxygen concentrator 100 may form a two-part molded plastic frame that includes, for example, two canisters 101 coupled to two compressors and an air delivery mechanism through multiple air pathways and valve seats 105*a-f* integrated into the frame. In some embodiments, the oxygen concentrator 100 may be formed out of a different number of molded components (e.g., one unitary component or using three or more components). Other techniques for forming the oxygen concentrator are also contemplated (e.g., laser sintering, machining, etc.).

In some embodiments, air pathways/tubing between different sections in the housing components 111*a,b* (e.g., between the canisters 101*a,b* and the oxygen accumulator 103) may take the form of molded channels. The tubing in the form of molded channels for air pathways may occupy multiple planes in the housing components 111*a,b* (e.g., may be formed at different depths and at different x,y,z positions in the housing components 111*a,b*). In some embodiments, a majority or substantially all of the tubing may be integrated into the molded housing (e.g., housing components 111*a,b*) to reduce potential leak points.

In some embodiments, prior to coupling the housing components 111*a,b* together, O-rings may be placed between various points of the housing components 111*a,b* (e.g., O-rings 135*a,b* between housing components 111*a* and 111*b* at tubes 121*a,b*). O-rings may also be placed between the ends of canisters 101*a,b* and the housing component 111*b* (which may function as a manifold) and between the end of the oxygen accumulator 103 and the housing component 111*b*. Other O-rings are also contemplated. In some embodiments, filters 207*a,b* may also be fastened (e.g., welded or using an adhesive) to the inside of the housing component 111*a* and/or 111*b* to prevent granules 139 from getting into the tubing/valves coupled to the canisters 101*a,b*. The filters 207 may also be welded onto either side of the spring baffles 701 to keep the granules 139 out of the tubing, etc. of housing component 111*b*. For example, the filter 207 may be welded onto the non-spring side of the spring baffle 701. The filters 207 may be spunbond filters made of one or more layers of textile cloth. Other filters are also contemplated. In some embodiments, the granules 139 may be added prior to coupling the housing components 111*a,b* together.

In some embodiments, components may be integrated and/or coupled separately to the housing components 111*a-b*. For example, tubing, flow restrictors (e.g., press fit flow restrictors), oxygen sensors (e.g., comprising an emitter 201 and receiver 203), granules 139 (e.g., zeolite), check valves 123, plugs, processors and other circuitry, battery 395, etc. may be coupled to the housing components 111*a-b* before and/or after the housing components 111*a-b* are coupled together. As disclosed, the oxygen concentrator 100 and components together may weigh less than 5 pounds and be smaller than 200 cubic inches. Other dimensions are also contemplated.

In some embodiments, apertures leading to the exterior of the housing components 111*a-b* may be used to insert devices such as flow restrictors. Apertures may also be used for increased moldability. One or more of the apertures may be plugged after molding (e.g., with a plastic plug). Plugs such as plug 125*a* and 125*b* may be used to plug apertures formed in housing component 111 to facilitate the injection molding process. In some embodiments, flow restrictors may be inserted into passages prior to inserting plug to seal the passage. For example, as seen in FIG. 6*g*, flow restrictor 321 may be a press-fit flow restrictor that is inserted into aperture 603*a* followed by a plug 127*a*. Flow restrictor 323 may be inserted into aperture 603*b* followed by plug 127*b*. Flow restrictor 325 may be inserted into aperture 603*e* followed by plug 127*e*. Other plugs may also be used (e.g., plug 127*c* (for aperture 603*c*), plug 127*d* (for aperture 603*d*), plug 127*f* (for aperture 603*f*), and plug 127*g* (for aperture 603*g*)). Press fit flow restrictors may have diameters that may allow a friction fit between the press fit flow restrictors and their respective apertures. In some embodiments, an adhesive may be added to the exterior of the press fit flow restrictors to hold the press fit flow restrictors in place once inserted. In some embodiments, the plugs may have a friction fit with their respective tubes (or may have an adhesive applied to their outer surface). The press fit flow restrictors and/or other components may be inserted and pressed into their respective apertures using a narrow tip tool or rod (e.g., with a diameter less than the diameter of the respective aperture). Other insertion mechanisms are also contemplated. In some embodiments, the press fit flow restrictors may be inserted into their respective tubes until they abut a feature in the tube to halt their insertion. For example, the feature may include a reduction in radius (e.g., see reduction 605 in FIG. 6G). Other features are also contemplated (e.g., a bump in the side of the tubing, threads, etc.). In some embodiments, press fit flow restrictors may be molded into the housing components 111*a,b* (e.g., as narrow tube segments).

Figure 7:
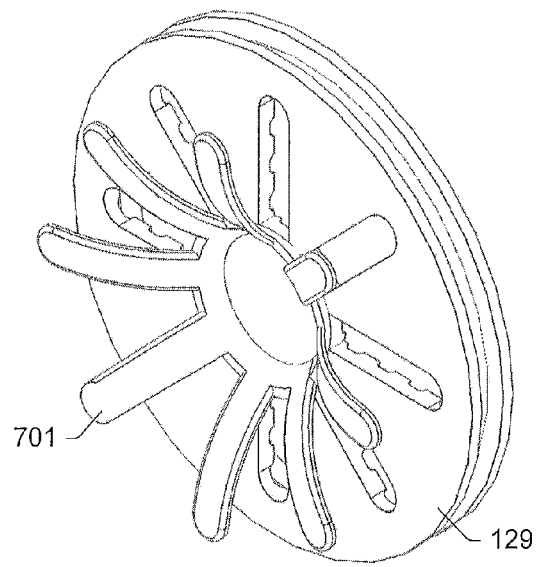
FIG. 7 illustrates a spring baffle, according to an embodiment.

In some embodiments, spring baffle 129 may be placed into respective canister receiving portions of the housing component 111*b* with the spring side of the baffle 129 facing the exit of the canister 101. In some embodiments, the spider legs 701 of the spring baffle 129 may engage the ridges 133 on the back of the canisters 101. FIG. 7 also illustrates an embodiment of the spring baffle 129. The spring baffle 129 may apply force to granules 139 in the canister 101 while also assisting in preventing granules 139 from entering the exit apertures 601*a,b*. The spring baffle 129 may keep the granules 139 compact while also allowing for expansion (e.g., thermal expansion). For example, during thermal expansion (or, for example, during a physical shock), spider legs 701 may compress. Keeping the granules 139 compact may prevent the granules 139 from breaking (e.g., during movement of the oxygen concentrator 100). The spring baffle 129 may be made of one piece molded plastic. Other materials and manufacturing techniques are also contemplated (e.g., stainless steel).

Figure 8:
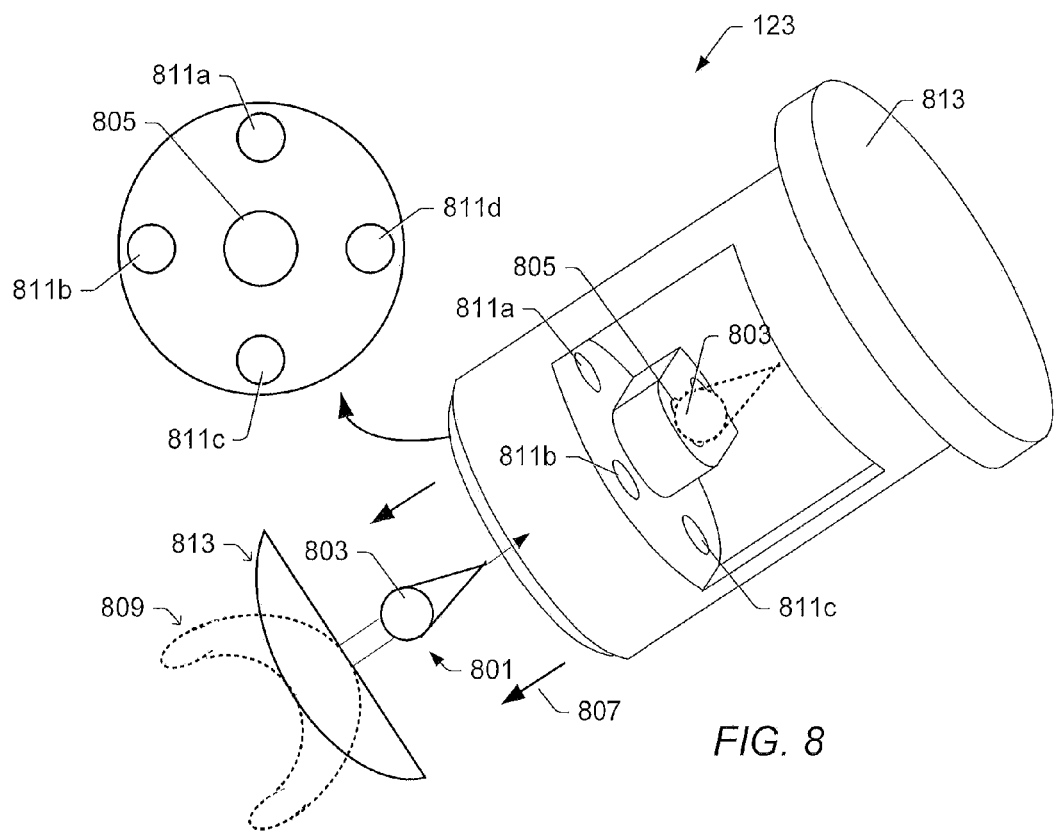
FIG. 8 illustrates a butterfly valve seat, according to an embodiment.

In some embodiments, check valves 123 may prevent oxygen from tube 121*a* or the oxygen accumulator 103 from entering tube 121*b* and may prevent oxygen from tube 121*b* and the oxygen accumulator 103 from entering tube 121*a*. In some embodiments, a butterfly check valve 123 may be used (other check valve types are also contemplated). FIG. 8 illustrates an embodiment of a butterfly check valve 123 (e.g., see butterfly valves 123*a,b* in FIG. 1) with a butterfly component 801. In some embodiments, the butterfly component 801 may be pulled into the valve seat 813 until the ball 803 of the butterfly component 801 snaps through the aperture 805 to hold the butterfly component 801 in place. As air flows in direction 807 through the check valve 123, (e.g., through apertures 811*a-d*) the butterfly component 801 may bend to allow air through the valve 123 (see configuration 809). If air tries to flow in the opposite direction (or if air flow is at rest), the butterfly component 801 may take configuration 813 to prevent air flow through the check valve 123.

In some embodiments, one or more compressors (e.g., two compressors 301*a,b*) may provide compressed air in a parallel arrangement. In some embodiments, dual-pump diaphragm compressors may be used for longer life (e.g., >20000 operating hours). Dual-pump diaphragm compressors may also work without needing additional oil. Dual-pump diaphragm compressors may also require less volume than larger single compressors used to compress a similar amount of air. Other compressors may also be used (e.g., a two stage compressor may be used).

In some embodiments, both compressors 301*a,b* may be used during normal operation (e.g., during normal user breathing rates/normal required oxygen flow rates). Air from the compressors 301 may enter the oxygen concentrator 100 through both inlets 109*a* and 109*b* and may be directed to a canister (e.g., canister 101*a* or 101*b*) through valves 305*a* and 305*b* (through respective valve seats 105*a*, 105*b*). At lower user breathing rates/lower required oxygen flow rates, a subset of the compressors 301 may be used. For example, only one compressor (301*a* or 301*b*) may be used and the air from the compressor 301*a* or 301*b* may enter through inlet 109*a* or 109*b*. The air may be similarly directed into a canister 101*a* or 101*b* through valves 305*a* and 305*b* (through respective valve seats 105*a*, 105*b*). In some embodiments, when a subset of the compressors 301 are operating, the subset that is operating may alternate operating time with the inactive compressors. For example, during single compressor operation, the two compressors 301 may alternate (e.g., to keep wear evenly distributed between the two compressors 301). In some embodiments, other numbers of compressors 301 may be used. For example, four compressors may be used during normal operation (e.g., with two compressors placing air into inlet 109*a* and two compressor placing air into inlet 109*b*). With four compressors, a subset of the compressors may include two operating compressors (e.g., either the two compressors placing air into inlet 109*a* or the two compressors placing air into inlet 109*b* or one compressor placing air into inlet 109*a* and one compressor placing air into inlet 109*b*). Other configurations are also contemplated. Using a subset of the compressors 301 may reduce power consumption during low activity times for the user (e.g., while the user is sitting). The reduced power consumption may allow for a smaller battery 395 to be used in the oxygen concentrator 100.

In some embodiments, a single compressor may be used (e.g., in different power modes). For example, during normal operation the compressor may be operated at full power, while, during lower breathing rates, the compressor may be operated at a lower power setting. In some embodiments, the compressors in multiple compressor operation may also be operated at different power levels (e.g., at lower power settings during lower breathing rates).

In some embodiments, if one or more of the compressors fails, the other compressors may provide at least a subset of the required oxygen to the user. This may provide oxygen to the user until the user can locate other oxygen arrangements. In some embodiments, one or more of the compressors may be redundant compressors such that if a compressor fails, the user may still receive the prescribed oxygen rate. In some embodiments, the redundant compressor may be activated when one of the active compressors fails. In some embodiments, the redundant compressor may have already been active (e.g., additional power may be supplied to the active compressors when one of the compressors fails).

Figure 26:
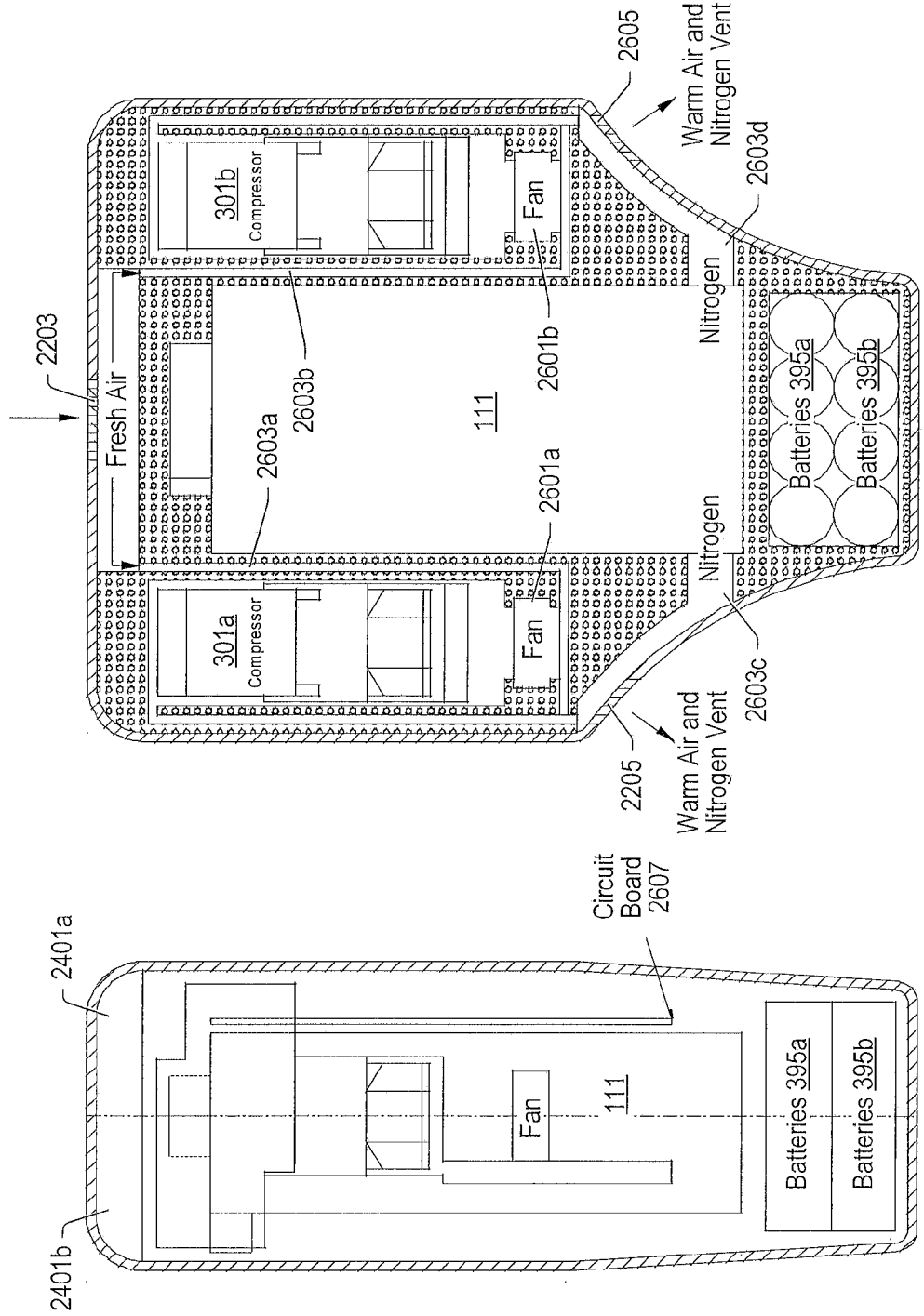
FIG. 26 illustrates a side and front profile of a component arrangement in the foam housings, according to an embodiment.

In some embodiments, the compressors 301 may be controlled through a compressor control system implemented by processor 399 (which may include, for example, one or more field programmable gate arrays (FPGAs), a microcontroller, etc. comprised on circuit board 2607 as seen in FIG. 26) executing programming instructions stored on memory 397. In some embodiments, the programming instructions may be built into processor 399 such that a memory 397 external to the processor 399 may not be separately accessed (i.e., the memory 397 may be internal to the processor 399). In some embodiments, the processor 399 may be coupled to the compressors 301. The processor 399 may also be coupled to other components of the oxygen concentrator (e.g., valves 305, oxygen sensor 307, demand transducer 331, etc.). In some embodiments, a separate processor (and/or memory) may be coupled to the other components of the oxygen concentrator 100. In some embodiments, the demand transducer 331 may be a pressure transducer 901 detecting inhalations to detect the breathing rate (and, for example, the volume). In some embodiments, the demand transducer 331 may be a separate transducer than the pressure transducer 901. The information from the demand transducer 331 may assist the processor 399 in making a determination as to how many compressors 301 should be operating. For example, if the user has a low breathing rate (e.g., less than an average breathing rate), the processor 399 may activate only a subset of the compressors 301 (e.g., one compressor). The user may have a low breathing rate if relatively inactive (e.g., asleep, sitting, etc.) as determined by comparing the detected breathing rate to a threshold. In some embodiments, the available compressors may be alternately used during low activity cycles to even out wear over the available compressors (instead of concentrating wear on one compressor). If the user has a relatively high breathing rate (e.g., at or more than an average breathing rate), the processor 399 may implement a greater number of compressors (e.g., both compressors 301*a-b*). The user may have a high breathing rate if relatively active (e.g., walking, exercising, etc.). The active/sleep mode may be determined automatically and/or the user may manually indicate a respective active or sleep mode (e.g., the user may press a button 2113 (active)/2115 (sleep) to indicate active or sleep mode (e.g., see FIG. 21b)). Other numbers of activity settings are also possible (e.g., low, moderate, active, and very active). Additional activity settings may use different numbers of subsets of compressors 301 (or different power levels for the operating compressors).

A user breathing at a rate of 30 breaths per minute (BPM) may consume two and one-half times as much oxygen as user who is breathing at 12 BPM. As noted above, if the breathing rate of the user is calculated and used to adjust the number of and/or power input to the compressors 301, less power may be used. For example, a user who is more active (e.g., walking) may consume more oxygen and require more power than the user who is less active (e.g., sitting or sleeping). In some embodiments, the breathing rate of the user may thus be detected and the bolus may be adjusted (e.g., by adjusting the power to or the operating number of the compressors 301) to provide more or less oxygen to allow the oxygen concentrator 100 to perform more efficiently by meeting the user's changing oxygen demands without operating at full power continuously. Using less power may reduce power consumption and increase battery life and/or decrease battery size requirements.

In some embodiments, if the user's current activity level (e.g., as determined using the detected user's breathing rate or some other factor such as airflow near the nasal cannula 903) exceeds a threshold (e.g., a predetermined threshold), the processor 399 may implement an alarm (e.g., visual and/or audio) to warn the user that the current breathing rate exceeds a safe operating threshold (and therefore, for example, the user may not be receiving a prescribed amount of oxygen). For example, the threshold may be set at 20 breaths per minute (other breathing thresholds are also contemplated). In some embodiments, the oxygen sensor 307 coupled to the oxygen concentrator 100 may measure an oxygen level (e.g., as percent oxygen) in the gas being delivered to the user and an alarm may be activated if the percent oxygen drops below a threshold. In addition, a gas flow meter 1143 may measure a volume of gas flowing to the user. The volume measurement and percent oxygen measurement may provide the volume of oxygen being delivered to the user and an alarm may be activated if the volume drops below a threshold. In some embodiments, an alarm may be activated if the percent and/or volume of oxygen exceeds a threshold (e.g., too much oxygen is being delivered to the user). In some embodiments, the processor 399 may implement several levels of alarms (e.g., colored lights to indicate the current demand on the oxygen concentrator 100). Alarms may also include auditory alarms and/or messages provided on LED (Light Emitting Diode) display 2105. In some embodiments, if the user's breathing rate exceeds the threshold and/or one or more compressors is inoperable, the operable compressors may be driven at a higher power setting (which may be only temporarily sustainable over an emergency period). Other compensation techniques are also contemplated.

In some embodiments, oxygen from the canisters 101 may be stored in an oxygen accumulator 103 in the oxygen concentrator 100 and released to the user as the user inhales. For example, the oxygen may be provided in a bolus in the first few milliseconds of a user's inhalation. The user's inhalation may be detected using a demand transducer (e.g., pressure transducer 901). In some embodiments, the size of the bolus may be reduced if the response time is decreased and, therefore, the oxygen needed to provide a prescribed flow rate for the user may also be reduced as response time is reduced. Releasing the oxygen to the user as the user inhales may prevent unnecessary oxygen generation (further reducing power requirements) by not releasing oxygen, for example, when the user is exhaling. Reducing the amount of oxygen required may effectively reduce the amount of air compressing needed for the oxygen concentrator 100 (and subsequently may reduce the power demand from the compressors). In some embodiments, the bolus may be 8 cubic centimeters (cc) to provide the equivalent of a prescribed 1 LPM (or 16 ccs for 2 LPM or 24 ccs for 3 LPM). Slower responses may require a larger bolus (e.g., 15 or 16 cc for a 1 LPM prescribed rate).

Figure 27:
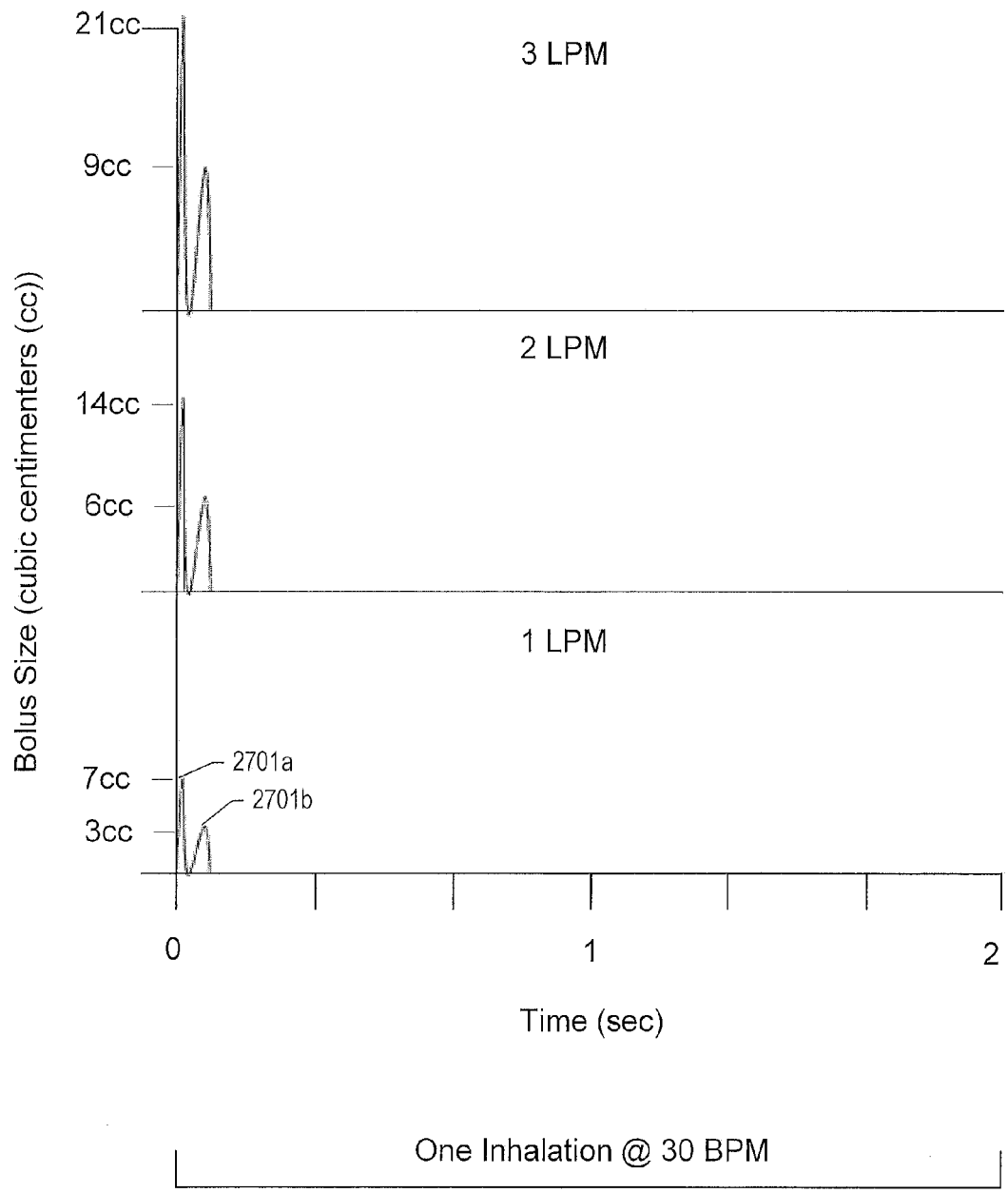
FIG. 27 illustrates three embodiments of gas mixture delivery profiles for the oxygen concentrator.

In some embodiments, as seen in FIG. 27, the bolus may include two or more pulses. For example, with a one liter per minute (LPM) delivery rate, the bolus may include two pulses: a first pulse 2701a at approximately 7 cubic centimeters and a second pulse 2701b at approximately 3 cubic centimeters. Other delivery rates, pulse sizes, and number of pulses are also contemplated. For example, at 2 LPMs, the first pulse may be approximately 14 cubic centimeters and a second pulse may be approximately 6 cubic centimeters and at 3 LPMs, the first pulse may be approximately 21 cubic centimeters and a second pulse may be approximately 9 cubic centimeters. In some embodiments, the larger pulse 2701a may be delivered when the onset of inhalation is detected (e.g., detected by demand transducer 331). In some embodiments, the pulses 2701 may be delivered when the onset of inhalation is detected and/or may be spread timewise evenly through the breath. In some embodiments, the pulses 2701 may be stair-stepped through the duration of the breath. In some embodiments, the pulses 2701 may be distributed in a different pattern. Additional pulses may also be used (e.g., 3, 4, 5, etc. pulses per breath). While the first pulse 2701a is shown to be approximately twice the second pulse 2701b, in some embodiments, the second pulse 2701b may be larger than the first pulse 2701a. In some embodiments, pulse size and length may be controlled by, for example, valve F 305g which may open and close in a timed sequence to deliver the pulses 2701. A bolus with multiple pulses 2701 may have a smaller impact on a user than a bolus with a single pulse. The multiple pulses 2701 may also result in less drying of a user's nasal passages and less blood oxygen desaturation. The multiple pulses 2701 may also result in less oxygen waste.

In some embodiments, silicone rubber tube 197 (FIG. 2a) may be compliant such that the diameter of the silicone rubber tube 197 may expand as the pulses 2701 travel through the silicone rubber tube 197 (and then return to a normal diameter between pulses 2701). The expansion may smooth out the pulses 2701 such that the pulses 2701 may be received by the user with a smoother peak. The smoother pulses may also be received by the user over a greater time period than the time period for the release of the boluses from valve 305g.

In various embodiments, the user's inhalation may be detected by using pressure transducer 901 on nasal cannula 903 detecting a negative pressure generated by venturi action at the start of a user's inhalation. The pressure transducer 901 may be operable to create a signal when the inhalation is detected to open a supply valve (e.g., valve 305g) to release an oxygen bolus from the oxygen accumulator 103. In some embodiments, the pressure transducer 901 may be located at the exit of oxygen concentrator 100 (e.g., see FIG. 9a) and may detect a pressure difference of the air in the tube 907. In some embodiments, the pressure transducer 901 may be located at the end of a tube 907 delivering oxygen to the user to detect a pressure difference at the user's nose. For example, the pressure transducer 901 may use Whetstone bridge microgauges to detect a pressure difference at the exit of the oxygen concentrator 100 or on the nasal cannula 903. Other placements of the pressure transducer 901 are also contemplated. Other pressure transducer types are also contemplated. In some embodiments, a plurality of pressure transducers may be used. In some embodiments, the pressure transducer 901 may be disposable.

In some embodiments, pressure transducers 901 may provide a signal that is proportional to the amount of positive or negative pressure applied to a sensing surface. The pressure transducers 901 may need to be sensitive enough to provide a predictable relationship between the output of the pressure transducers 901 and the signal the pressure transducers 901 deliver. In some embodiments, the processor 399 may use information from the pressure transducer 901 to control when the bolus of oxygen should be released. The processor 399 may also control other components based on information from the pressure transducer 901 (e.g., the sensitivity of the pressure transducer 901, the number of active compressors 301 and/or the power level of the compressors 301, etc.).

In some embodiments, the sensitivity of the pressure transducer 901 may be affected by the physical distance of the pressure transducer 901 from the user, especially if the pressure transducer 901 is located on the oxygen concentrator 100 and the pressure difference is detected through the tubing 907 to the nasal cannula 903. In some embodiments, the pressure transducer sensitivity may not be affected by the length of the tubing 907 because the pressure transducer 901 may be placed in the mask or nasal cannula 903 (e.g., see FIG. 9b) and a signal from the pressure transducer 901 may be delivered to a processor 399 in the oxygen concentrator 100 electronically via wire 905 (which may be co-extruded with the tubing 907) or through telemetry such as through Bluetooth™ or other wireless technology (e.g., using a wireless transmitter at the pressure transducer 901 and a wireless receiver at the oxygen concentrator 100). Placing the pressure transducer 901 on the nasal cannula 903 may allow for a longer delivery tube 907. In some embodiments, the pressure transducer 901 may be placed near a prong on the nasal cannula used to deliver oxygen into the user's nose.

In some embodiments, a dual lumen tube 909 may be used. One lumen (e.g., see cross section of lumens 911a, 911b, or 911c) may deliver the oxygen to the user and one lumen 913 (e.g., see cross section of lumens 913a, 913b, or 913c) may have a smaller diameter than the first lumen 911 and may transfer a pressure difference to the pressure transducer 901 mounted in the pressure transducer 901 at the oxygen concentrator 100. With a smaller diameter, the second lumen 913 may reduce the volume of air between the user and the pressure transducer 901 for a given length of tubing. As the volume of air is reduced, compliance of a pressure spike delivery medium may be reduced and the sensitivity of the pressure transducer 901 may correspondingly be increased. For example, the pressure difference in lumen 913 resulting from a user's inhalation may be easier to detect at the pressure transducer 901 at the oxygen concentrator 100 than if the pressure difference were being detected through a lumen with a greater diameter. In some embodiments, the detectable pressure difference may decrease along the length of the lumen such that at a certain length of lumen, the pressure difference may not be detectable. Reducing the diameter of the lumen may result in the pressure difference being easier to detect at farther distances (i.e., because there is less air in the lumen to transmit the pressure difference and, correspondingly, less transporting air volume to weaken the pressure difference). The pressure difference may also be detectable more quickly in a narrow diameter lumen than in a lumen with a greater diameter. In some embodiments, the dual lumen 909 may take on the configuration shown in FIG. 9d or 9e. Other configurations are also contemplated. In some embodiments, the dual lumens 909 may be co-extruded plastic. Other manufacturing techniques and materials are also contemplated.

Figure 10:
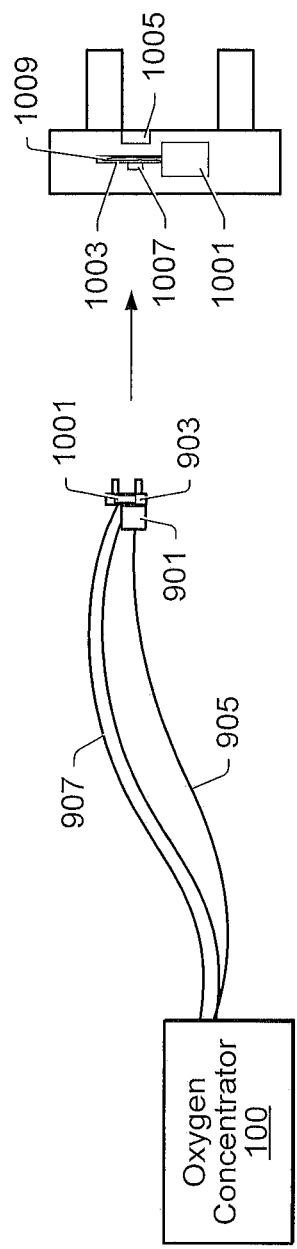
FIG. 10 illustrates a hall effect pressure transducer and associated hose configuration, according to an embodiment.

Pressure transducer 901 may detect a pressure difference and/or a quantitative measurement of the inhalation pressure drop. Detecting the user's inhalation may not require a quantitative measurement of the inhalation pressure difference, but may rely on a temporal indicator to sense the inhalation. In some embodiments, devices other than or in addition to pressure transducers 901 may be used to detect a user's inhalation. For example, in some embodiments, a Hall-effect sensor 1001 (see FIG. 10) may be used to detect a user's inhalation. The Hall-effect sensor 1001 may include a vane 1003 with a magnet 1007 on the vane 1003. The vane 1003 may be positioned in the nasal cannula 903 and a second magnet 1005 (e.g., a rare earth magnet) may be arranged to assist in detection of movement of the magnet 1007 on the vane 1003 (using the Hall-effect) relative to the Hall-effect sensor 1001. For example, when the vane 1003 is detected moving toward the second magnet 1005 (e.g., through the effect on a current in wire 1009 to the changing magnetic field), the sensor 1001 may indicate a negative pressure (which may correspond to the beginning of a user inhalation). For example, air movement toward the user's nose as the user begins taking a breath may move the vane 1003 toward the second magnet 1005. The Hall-effect sensor 1001 may provide a more sensitive detector of the time the inhalation begins in the users breathing cycle. In some embodiments, the signal from the Hall-Effect sensor 1001 may be sent down wire 905 (or wirelessly transmitted). Other magnet-based sensors may also be used (e.g., a small magnet moved by the user's inhalation that acts to close a circuit). Other Boolean type sensors may be used.

In some embodiments, the sensitivity of the oxygen concentrator 100 may be selectively attenuated to reduce false inhalation detections due to movement of air from a different source (e.g., movement of ambient air). For example, the oxygen concentrator 100 may have two selectable modes—an active mode and an inactive mode. In some embodiments, the user may manually select a mode (e.g., through a switch or user interface). In some embodiments, the mode may be automatically selected by the oxygen concentrator 100 based on a detected breathing rate. For example, the oxygen concentrator 100 may use the pressure transducer 901 to detect a breathing rate of the user. If the breathing rate is above a threshold, the oxygen concentrator 100 may operate in an active mode (otherwise, the oxygen concentrator may operate in an inactive mode). Other modes and thresholds are also contemplated.

In some embodiments, in active mode, the sensitivity of the pressure transducer 901 may be mechanically, electronically, or programmatically attenuated. For example, during active mode, the processor 399 may look for a greater pressure difference to indicate the start of a user breath (e.g., an elevated threshold may be compared to the detected pressure difference to determine if the bolus of oxygen should be released). In some embodiments, the pressure transducer 901 may be mechanically altered to be less sensitive to pressure differences. In some embodiments, an electronic signal from the pressure transducer 901 may be electronically attenuated to indicate a smaller pressure difference than detected at the pressure transducer 901 (e.g., using a transistor). In some embodiments, during the inactive mode the sensitivity of the pressure transducer 901 may not be attenuated (e.g., the sensitivity of the pressure transducer 901 may be increased during sleep periods). For example, the processor 399 may look for a smaller pressure difference to indicate the start of a user breath (e.g., a smaller threshold may be compared to the detected pressure difference to determine if the bolus of oxygen should be released). In some embodiments, with increased sensitivity, the response time for delivery of the bolus of oxygen during the user's inhalation may be reduced. The increased sensitivity and smaller response time may reduce the size of the bolus necessary for a given flow rate equivalence. The reduced bolus size may also reduce the size and power consumption of the oxygen concentrator 100 that may reduce the size of a battery 395 needed to operate the oxygen concentrator (which may make the oxygen concentrator smaller and more portable).

FIG. 11 illustrates a circuit diagram of an ultrasonic sensor assembly, according to an embodiment. In some embodiments, the oxygen sensor 307 may be an ultrasonic sensor that may be used to measure an oxygen level or the percent oxygen in the gas being delivered to the user. Other uses of the ultrasonic sensor assembly are also contemplated (e.g., to detect/measure the presence of other gases for other devices). An ultrasonic sound wave (from emitter 201) may be directed through a chamber 1101 containing a sample of the gas mixture (e.g., from the supply line providing oxygen to the user) to receiver 203. The sensor 307 may be based on detecting the speed of sound through the gas mixture to determine the composition of the gas mixture (e.g., the speed of sound is different in nitrogen and oxygen). In a mixture of the two gases, the speed of sound through the mixture may be an intermediate value proportional to the relative amounts of each in the mixture. In some embodiments, the concentration of oxygen may be determined by measuring the transit time between an emitter 201 and the receiver 203. In some embodiments, multiple emitters 201 and receivers 203 may be used. Emitters 201 may be axially aligned with respective receivers 203. Other configurations are also contemplated. The readings from the emitters 201 and receivers 203 may be averaged to cancel errors that may be inherent in turbulent flow systems. In some embodiments, the presence of other gases may also be detected by measuring the transit time and comparing the measured transit time to predetermined transit times for other gases and/or mixtures of gases.

In some embodiments, a zero-crossing point of the sound wave 1205 may be used as a reference point for these measurements (other points may also be used). The sensitivity of the sensor 307 may be increased by increasing the distance between the emitter 201 and receiver 203 (e.g., to allow several sound wave cycles to occur between the emitter 201 and the receiver 203). In some embodiments, if at least two sound cycles are present, the influence of structural changes of the transducer may be reduced by measuring the phase shift relative to a fixed reference at two points in time. If the earlier phase shift is subtracted from the later phase shift, the shift caused by thermal expansion of the transducer housing may be reduced or cancelled. The shift caused by a change of the distance between the emitter 201 and receiver 203 may be the approximately the same at the measuring intervals, whereas a change owing to a change in oxygen concentration may be cumulative. In some embodiments, the shift measured at a later time may be multiplied by the number of intervening cycles and compared to the shift between two adjacent cycles.

Figure 12:
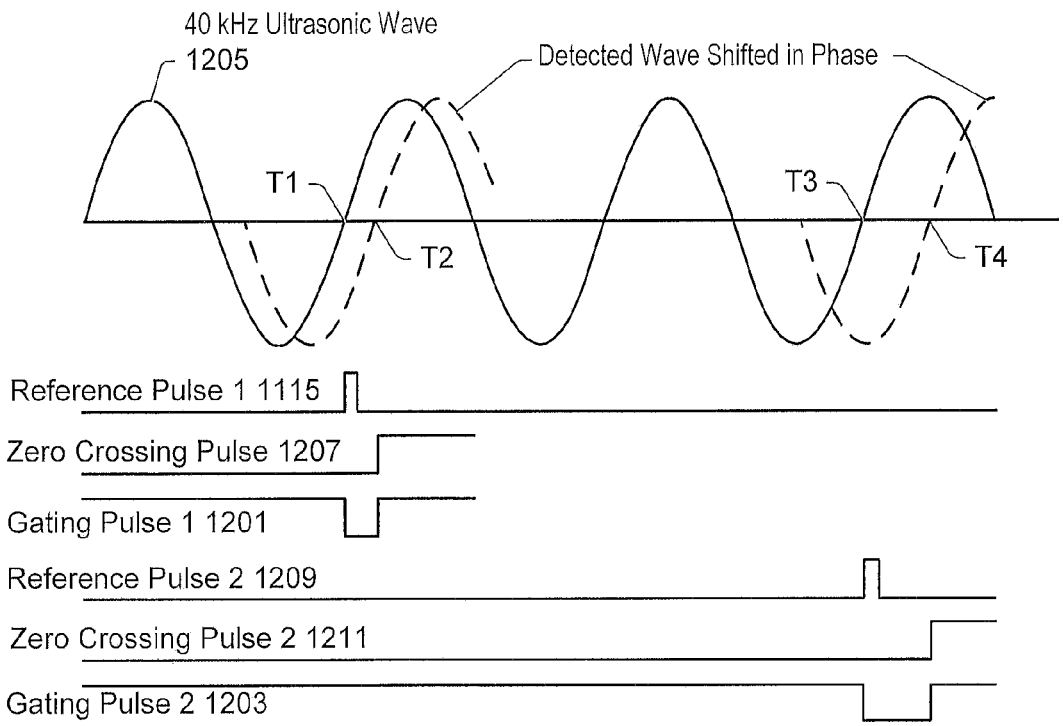
FIG. 12 illustrates a shifted wave pulse as detected by the ultrasonic sensor assembly, according to an embodiment.
Figure 14:
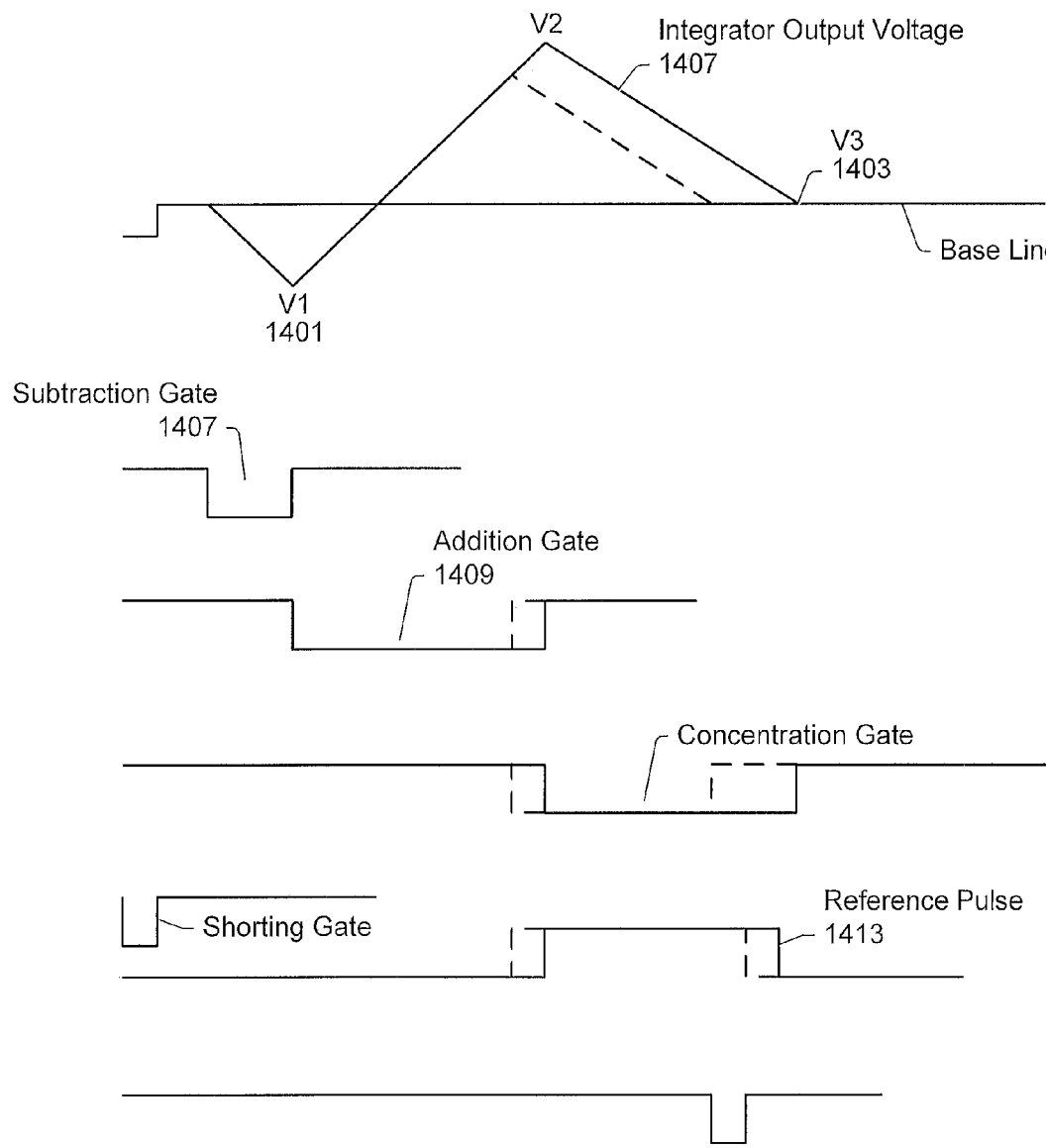
FIG. 14 illustrates various gates for the ultrasonic sensor, according to an embodiment.

In some embodiments, a pulse generator 1103 may send an enable pulse 1105 to a NAND gate U2 1107, which may channel a 40 kHz excitation signal to the emitter 201, via amplifier U1 1109. Other excitations signals are also contemplated. After traversing the gaseous mixture in the chamber 1101, the ultrasonic sound wave may impinge on the receiver 203, and in the process, may undergo a phase shift, relative to the excitation signal. The gas may be introduced (prior to or during the sound wave transmission) into the chamber 1101 via ports 1131a,b that are perpendicular to the direction of the sound wave. The velocity-induced components of the phase shift may be reduced or cancelled. Turbulence may create a uniform gaseous mixture in the chamber 1101. A change in the composition of the gas may affect the sound velocity of the sound wave traveling between the emitter 201 and the receiver 203. A higher concentration of oxygen may correspond to a lower sound velocity (and, correspondingly, more phase shift). The sound wave captured by the receiver 203 may be amplified by U3 1111 and put into a zero-crossing detector U4 1113 (which may provide zero crossing pulse 1207 to flip-flop U5 1117). The pulse generator 1103 may provide reference pulse 1 1115 to flip-flop U5 1117, clear the flip-flop U5 1117 and the output 1207 of the zero-crossing detector 1113, and create a negative-going pulse to gate pulse 1 1201, as shown in FIG. 12. The length of this pulse may correspond to the phase shift occurring in the interval T2–T1. In an analogous fashion, gating pulse 2 1203 may be derived in the interval T4–T3 (e.g., with reference pulse 2 1209 and zero crossing pulse 2 1211 provided to flip-flop U6 1135). Phase shifts caused by structural changes in the transducer housing may be reduced or cancelled by subtracting interval T2–T1 from interval T4–T3. An embodiment of the process is illustrated in FIG. 14. The integrator 1133 may be zeroed to reduce or eliminate drift that may have accrued since the last operation. Then, the subtraction gate 1407 may be opened by gating pulse 1 1201. After the gate has closed, the voltage at the integrator output may be V1 (see 1401 in FIG. 14):

$$V1 = K1 \times (St + Sc)$$

(where St is the phase shift caused by temperature 1301, Sc is the phase shift caused by changes in oxygen concentration 1303, and $K1 = t/RC \times (-Vref)$, where RC is a reflection coefficient and Vref is the reference voltage). After the gate has closed, the integrator output 1407 may remain stable until the addition gate 1409 opens. (The flat sections in the figure have been omitted for clarity.) After the termination of the addition gating pulse, the output voltage may be V2 (see 1403 in FIG. 14):

$$V2 = K1 \times [(St + Sc) - (St + 2 \times Sc)] = K1 \times Sc$$

Termination of the addition gate may clear flip-flop U7 1119, which may output a gating pulse that opens the calibrating gate, U8C 1121. U7 1119 may be set by U4 1113, when V3=0 (see 1403):

$$V3 = V2 - K2 \times t = 0; \; K1 \times Sc = K2 \times t; \; t = K1/K2 \times Sc$$

Figure 13:
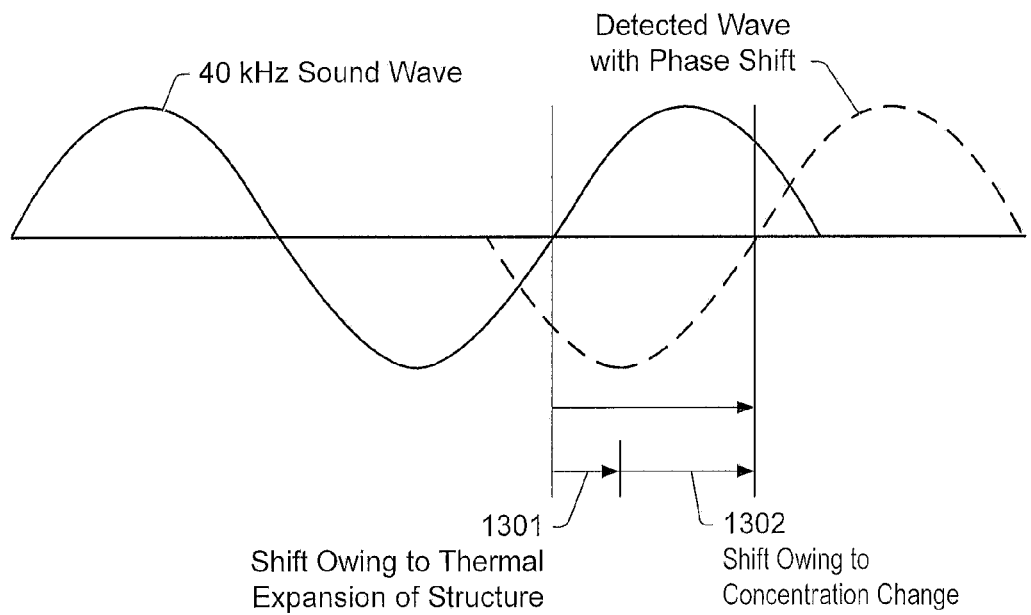
FIG. 13 illustrates the components of the shift for the oxygen concentrator, according to an embodiment.

(where $K2 = t/RC \times (+Vref)$). The length of the negative-going pulse from U7 1119 may be proportional to the phase shift Sc. An embodiment of the relationship between St and Sc is shown in FIG. 13. The pulse generator shown in FIG. 11 may issue a concentration reference pulse 1413 whose length is set to correspond to, for example, the minimum acceptable oxygen concentration (e.g., as defined by the user's prescription or other source). As shown in FIG. 14, low oxygen concentration may cause the zero crossing to occur earlier and make both inputs of U11 1123 high at the same time. The resulting pulse may be used to activate an audible alarm 1139 (through amplifier U12 1141) to alert the user that the oxygen concentration may be too low. The point at which the alarm is triggered may be set by adjusting P2 1125, (e.g., see FIG. 11). The velocity of sound may increase with temperature (which may incorrectly indicate a decrease in oxygen concentration). This effect may be reduced or cancelled by using a thermistor 1127 whose resistance increases with temperature to restore the duration of the concentration pulse to a corrected value. The amount of correction introduced may be varied by adjusting P1 1129. FIG. 6*a-h* shows the sensor constructed with discrete components. In some embodiments, the processing may be performed by a processor 399 (e.g., a field programmable gate array (FPGA)).

In some embodiments, the oxygen sensor 307 may include a gas flow meter 1143 that uses the Doppler effect to measure the volume of gas flow past the sensor. With the volume measurement from the gas flow meter 1143 and the percent oxygen reading from the ultrasonic sensor, the amount of oxygen delivered to the user may be measured and controlled. For example, if the concentration of oxygen is greater than a desired percentage, (e.g., as indicted by the length of the concentration reference pulse 1413), then the user is receiving at least a volume of oxygen equal to the volume of gas flow*the desired percentage of oxygen. In some embodiments, one or more signals from the ultrasonic sensor may be relayed to the processor 399 for a determination of an actual percentage of oxygen in the sample. For example, the processor 399 may receive an indication of gating pulse 1201, gating pulse 1203, and/or concentration reference pulse 1413 to determine an approximate percentage of oxygen in the gas sample. Other signals may also be used. Using a gas flow meter 1143 that uses the Doppler effect to measure the volume of gas flow may be more accurate than simply using time, pressure and orifice size to determine delivered volume.

Figure 15:
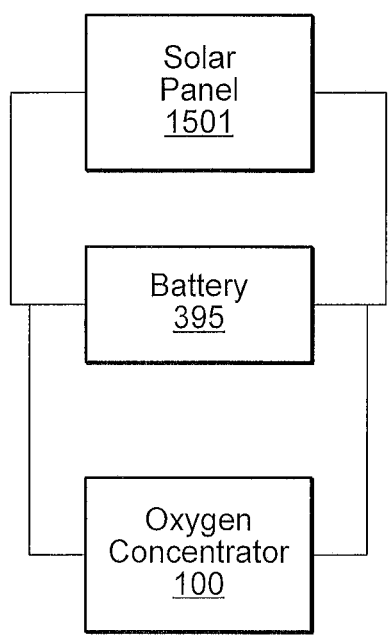
FIG. 15 illustrates a solar panel coupled to the oxygen concentrator, according to an embodiment.

In some embodiments, the battery 395 may be a rechargeable lithium battery. Other battery types are also contemplated. Larger batteries may be used for longer battery life. Smaller batteries may have a shorter battery life, but may be lighter. In some embodiments, a battery large enough to provide a battery life of 2 hours (using the various power saving mechanisms discussed herein) may be used. Other battery lifetimes/sizes are also contemplated. As seen in FIG. 15, in some embodiments, additional power may be provided to the oxygen concentrator 100 through a solar powered recharging circuit including solar panel 1501 so that the battery 395 may be supplemented to increase battery life or reduce battery size (e.g., especially while the user may be consuming more oxygen (and thus more power) outdoors). In some embodiments, an alternating current power adapter may be provided to charge the battery and/or provide power to the oxygen concentrator. Other power sources are also contemplated (e.g., an adapter to allow the oxygen concentrator to be plugged into a power outlet in an automobile).

Figure 16:
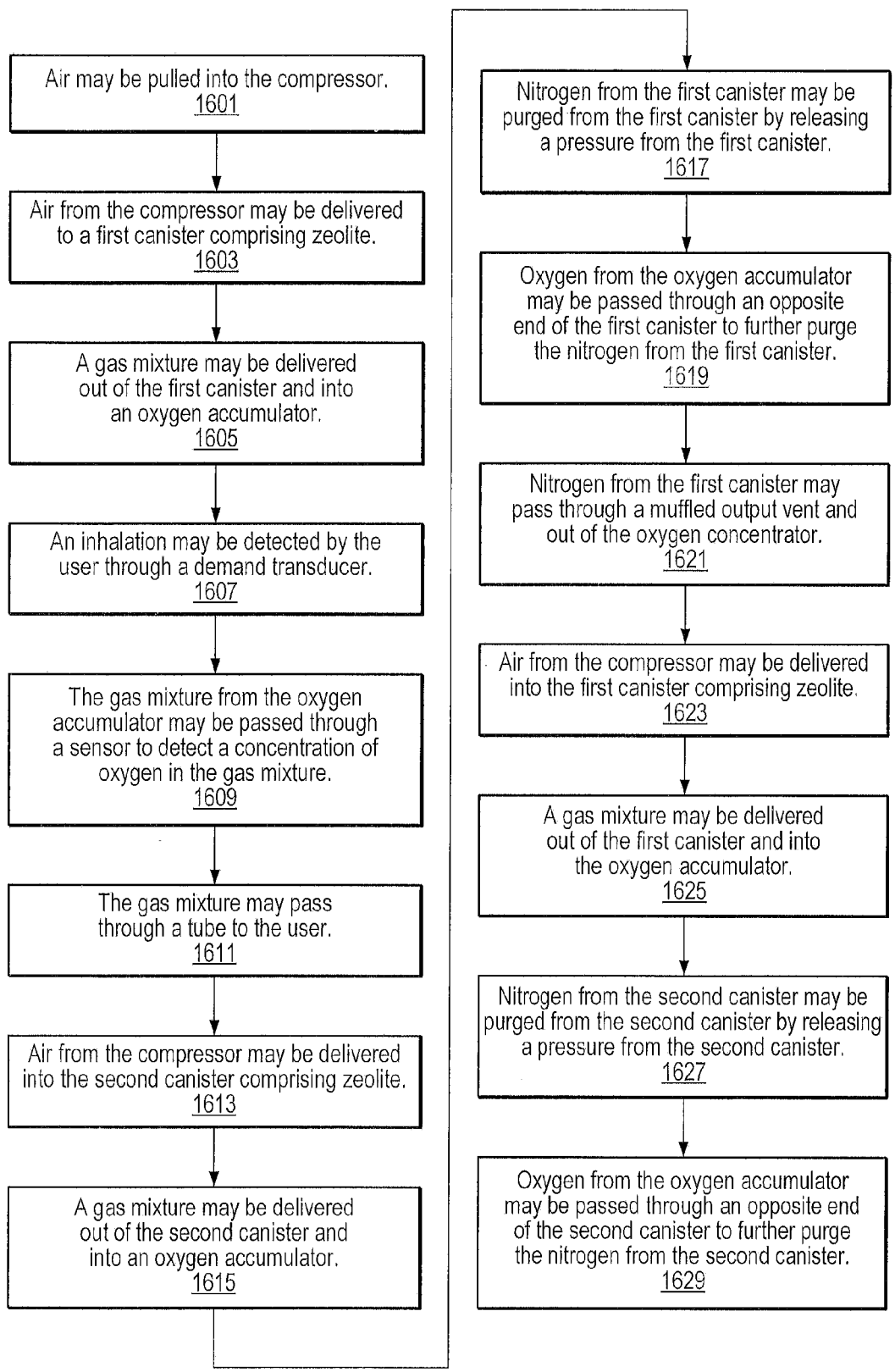
FIG. 16 illustrates a flowchart of an embodiment for oxygen concentrator operation, according to an embodiment.

FIG. 16 illustrates a flowchart of an embodiment for oxygen concentrator operation, according to an embodiment. It should be noted that in various embodiments of the methods described below, one or more of the elements described may be performed concurrently, in a different order than shown, or may be omitted entirely. Other additional elements may also be performed as desired.

At 1601, air may be pulled into the compressor 301. The compressor may include, for example, dual-pump diaphragm compressors 301*a-b*. The air may pass through a moisture and sound absorbing muffler 393 prior to entering the compressor 301. For example, a water absorbent (such as a polymer water absorbent) may be used. Other absorbents may also be used.

At 1603, air from the compressor 301 may be delivered to a first canister 101*a* comprising zeolite 391. The air from the compressor 301 may be directed through one or more valves 305 on the path to the first canister 101*a*. The valves 305 may be coupled to and controlled by a microprocessor (e.g., processor 399).

At 1605, a gas mixture (which may be comprised of mainly oxygen) may be delivered out of the first canister 101*a* and into an oxygen accumulator 103. In some embodiments, the gas mixture may pass through a check valve 123*a* (e.g., a butterfly check valve) between the first canister 101*a* and the oxygen accumulator 103. In some embodiments, a pressure transducer 389 may detect a pressure of the oxygen accumulator 103. The pressure of the oxygen accumulator may be used, for example, by the processor to determine if one or more of the canisters has a leak, etc. Other uses for the pressure are also contemplated.

At 1607, an inhalation may be detected by the user through a demand transducer 331 (e.g., pressure transducer 901).

At 1609, the gas mixture from the oxygen accumulator 103 may be passed through an oxygen sensor 307 (e.g., an ultrasonic sensor) to detect a concentration of oxygen in the gas mixture. The sensor may also include or be coupled to a gas flow meter 1143 to detect a volume of the gas passing the gas flow meter 1143.

At 1611, the gas mixture may pass through a tube (e.g., tube 907 or tube 909) to be delivered to the user through a nasal cannula 903. In some embodiments, the gas mixture may be delivered to the user in a single pulse or in two or more pulses (e.g., see FIG. 27).

At 1613, air from the compressor 301 may be delivered into the second canister 101*b* comprising zeolite 391.

At 1615, a gas mixture (which may be comprised of mainly oxygen) may be delivered out of the second canister 101*b* and into the oxygen accumulator 103.

At 1617, nitrogen from the first canister 101*a* may be purged from the first canister 101*a* by releasing a pressure (e.g., by opening valve 305*c* or 305*d* (and closing valves 305*a* and 305*b*) to open up an air pathway between the first canister 101*a* and the output vent 327) from the first canister 101*a*.

At 1619, oxygen from the oxygen accumulator 103 may be passed through an opposite end of the first canister 101*a* to further purge the nitrogen from the first canister 101*a*.

At 1621, nitrogen from the first canister 101*a* may pass through a muffled output vent 327 and out of the oxygen concentrator 100.

At 1623, air from the compressor 301 may be delivered into the first canister 101*a* comprising zeolite 391.

At 1625, a gas mixture (which may be comprised of mainly oxygen) may be delivered out of the first canister 101*a* and into an oxygen accumulator 103.

At 1627, nitrogen from the second canister 101*b* may be purged from the second canister 101*b* by releasing a pressure from the second canister 101*b*.

At 1629, oxygen from the oxygen accumulator 103 may be passed through an opposite end of the second canister 101*b* to further purge the nitrogen from the second canister 101*b*.

Figure 17:
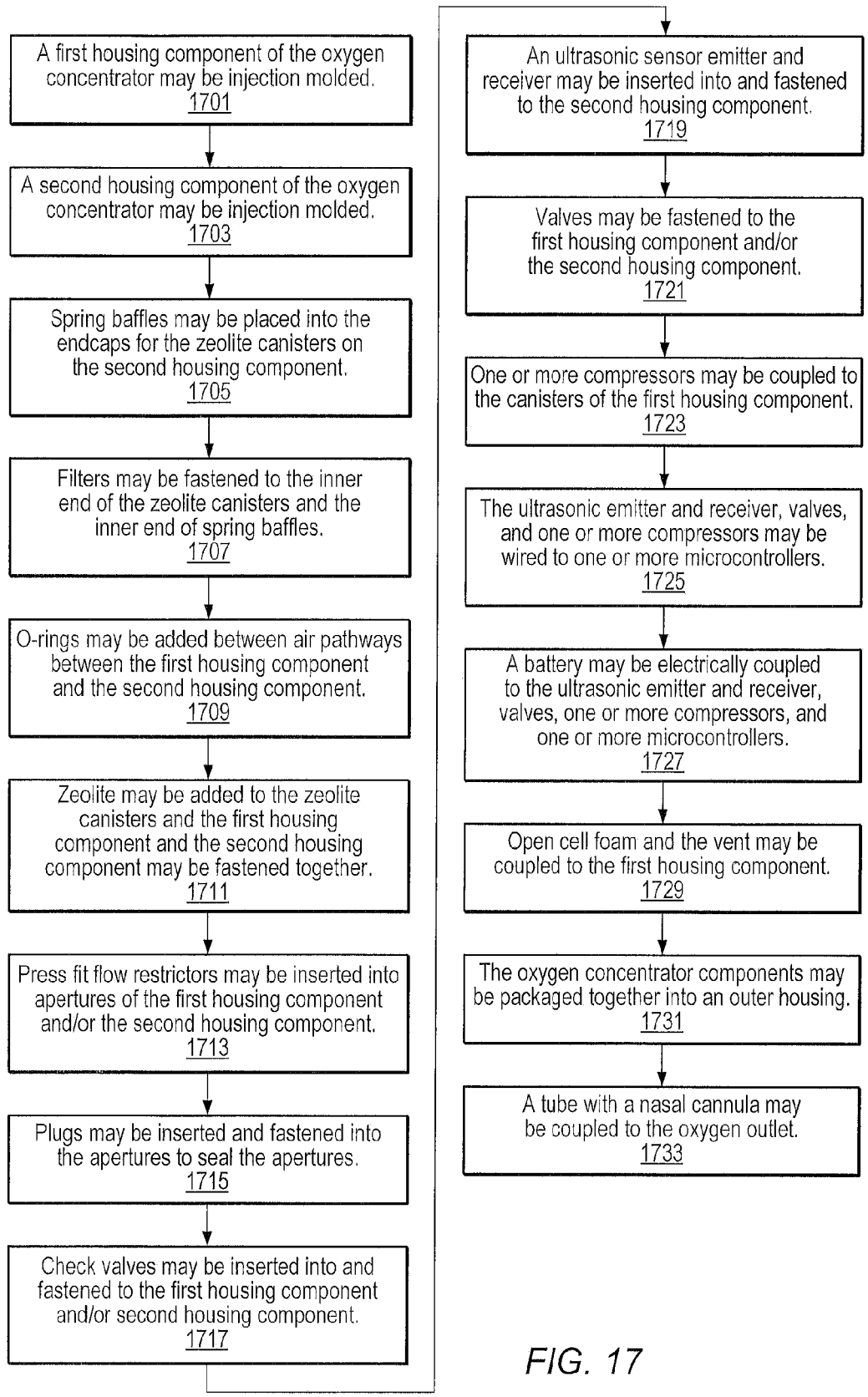
FIG. 17 illustrates a flowchart of an embodiment for oxygen concentrator assembly, according to an embodiment.

FIG. 17 illustrates a flowchart of an embodiment for oxygen concentrator assembly, according to an embodiment. It should be noted that in various embodiments of the methods described below, one or more of the elements described may be performed concurrently, in a different order than shown, or may be omitted entirely. Other additional elements may also be performed as desired.

At 1701, a first housing component 111*a* of the oxygen concentrator 100 may be injection molded. The first housing component 111*a* may include internal air pathways and zeolite canisters 101. In some embodiments, an inverted mold may be formed (with solid portions corresponding to the air pathways/inner canisters of the first housing component 111*a*) and placed inside a container with an inner shape with dimensions similar to the outer dimensions of the first housing component 111*a*. Spacers may be added between the solid portions and the container to hold the solid portions relative to the container. A plastic (e.g., a liquid thermoplastic) may be injected into the spaces between the outer container and the solid portions to form the injection molded first housing component 111*a*. The mold (comprising the container and solid portions) may then be removed and/or broken away. In some embodiments, the mold may be melted away from the injection molded first housing component 111*a* after the injection molded first housing component 111*a* has cooled. Other methods of injection molding are also contemplated. Other molding techniques are also contemplated.

At 1703, a second housing component 111*b* of the oxygen concentrator 100 may be injection molded. The second housing component 111*b* may include internal air pathways and endcaps for the zeolite canisters 101.

At 1705, spring baffles 129 may be placed into the endcaps for the zeolite canisters on the second housing component 111*b*. In some embodiments, the spider legs 701 of the spring baffle 129 may engage the ridges 133 on the back of the canisters 101*a,b*.

At 1707, filters (e.g., filters 207) may be fastened to the inner end of the zeolite canisters on the first housing component 111*a* and the inner end (end without the spider legs) of spring baffles 129 in the second housing component 111*b*.

At 1709, O-rings 135 may be added between air pathways 121 between the first housing component 111*a* and the second housing component 111*b*. For example, O-rings 135 may be placed between the endcaps for the zeolite canisters 101 on the second housing component 111*b* and the zeolite canisters 101 on the first housing component 111*a*. Other O-rings may also be used.

At 1711, zeolite 391 may be added to the zeolite canisters 101 and the first housing component 111*a* and the second housing component 111*b* may be fastened together (e.g., through an adhesive, solvent weld, etc.).

At 1713, press fit flow restrictors (e.g., press fit flow restrictors 311, 321, 323, and 325) may be inserted into apertures (e.g., formed during the injection molding process) of the first housing component 111*a* and/or the second housing component 111*b*.

At 1715, plugs (e.g., plugs 127) may be inserted and fastened into the apertures to seal the apertures. For example, the plugs may be fastened through the use of an adhesive or solvent weld. Other fastening techniques are also contemplated.

At 1717, check valves 123 may be inserted into and fastened (e.g., through an adhesive) to the first housing component 111*a* and/or second housing component 111*b*.

At 1719, an ultrasonic sensor emitter 201 and receiver 203 may be inserted into and fastened to the second housing component. For example, the ultrasonic sensor emitter 201 and receiver 203 may be coupled to the second housing component through an adhesive or friction fit. In some embodiments, multiple ultrasonic sensor emitters 201 and ultrasonic receivers 203 may be used. Emitters 201 may be axially aligned with respective receivers 203 such that the gas flows perpendicular to the axis of alignment. Other configurations are also contemplated.

At 1721, valves (e.g., valves 305) may be fastened to the first housing component 111*a* and/or the second housing component 111*b* (e.g., screwed onto the exterior). Other fastening techniques for the valves are also contemplated (e.g., adhesive).

At 1723, one or more compressors 301 may be coupled to the canisters 101 of the first housing component (e.g., through one or more tubes 199 coupled to valves 305 coupled to the first housing component).

At 1725, the ultrasonic emitter 201 and receiver 203, valves, and one or more compressors may be wired to one or more microcontrollers (e.g., processor 399). Other electronic components may also be coupled to the microcontrollers. For example, an on/off button 2103*a,b* and an LED display 2105*a,b* (see FIGS. 21*a,b*) to convey information such as low oxygen or low power warnings to the user.

At 1727, a battery 395 may be electrically coupled to the ultrasonic emitter 201 and receiver 203, valves, one or more compressors 301, and one or more microcontrollers. The battery 395 may also be electrically coupled to other components of the oxygen concentrator 100. In some embodiments, the battery 395 may be electrically coupled to components of the oxygen concentrator 100 through other components (e.g., the battery 395 may be coupled to the valves 305 through the processor 395).

At 1729, open cell foam and the vent 401 may be coupled to the first housing component 111*a* (e.g., the foam may be inserted into the vent out 137 and vent 401 may be fastened over the vent out 137 through, for example, an adhesive).

Figure 21A:
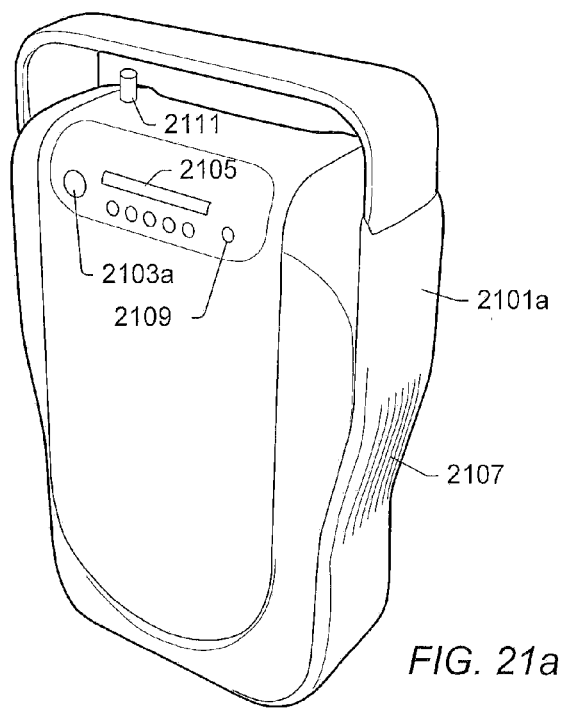
FIGS. 21a-c illustrate outer housings, according to two embodiments.

At 1731, the oxygen concentrator components (e.g., first housing component 111*a*, second housing component 111*b*, battery 395, compressors 301, etc.) may be packaged together into an outer housing 2101*a,b* (e.g., see FIGS. 21*a,b*). In some embodiments, the outer housing 2101 may be a durable, light-weight plastic. Other materials are also contemplated. Other outer housing configurations are also contemplated. In some embodiments, the components may be placed in an foam housings 2401 (see FIGS. 24-25) and the foam housings 2401 may be placed inside an enclosure housing 2201 before being placed inside outer housing 2101.

At 1733, a tube (e.g., tube 907 or 909) with a nasal cannula 903 may be coupled to the oxygen outlet 107. If a dual lumen is used, lumen 913 may be coupled to a pressure transducer 901 coupled to the oxygen concentrator 100.

Figure 18:
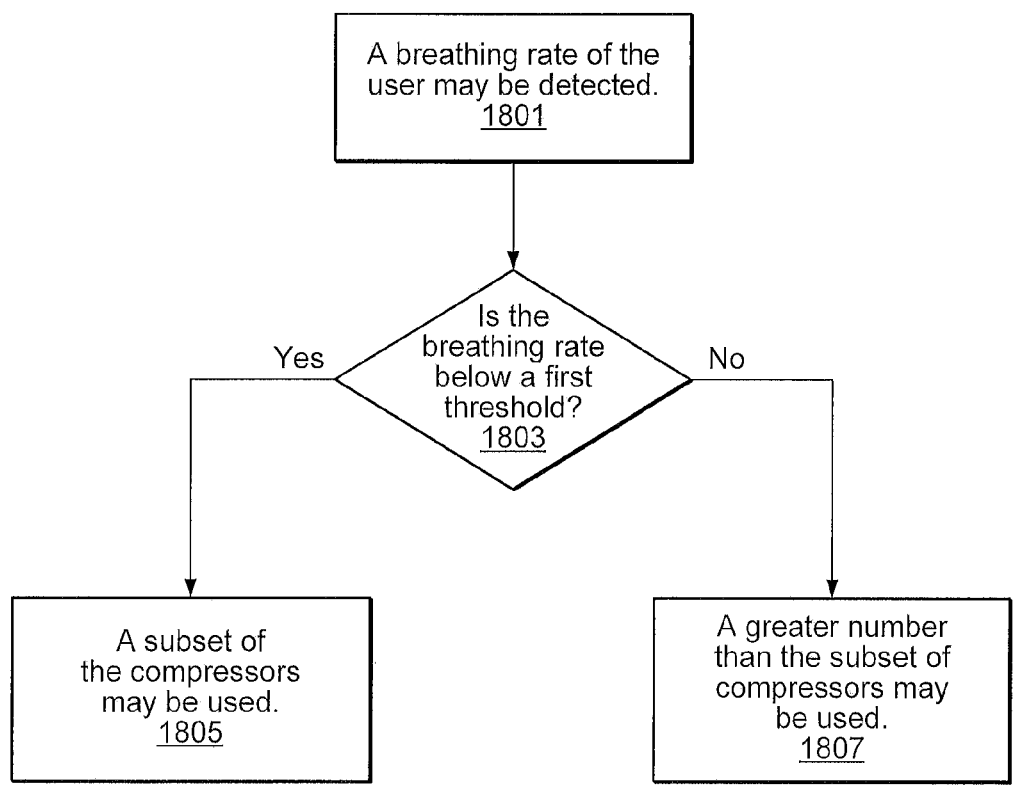
FIG. 18 illustrates a flowchart of an embodiment for compressor control, according to an embodiment.

FIG. 18 illustrates a flowchart of an embodiment for compressor control, according to an embodiment. It should be noted that in various embodiments of the methods described below, one or more of the elements described may be performed concurrently, in a different order than shown, or may be omitted entirely. Other additional elements may also be performed as desired.

At 1801, a breathing rate of the user may be detected (e.g., by determining how may inhalations pressure sensor 901 detects per minute).

At 1803, a determination may be made as to whether the breathing rate is below a first threshold. The first threshold may be, for example, 15 breaths per minute (other thresholds are also contemplated). In some embodiments, the threshold may be predetermined and/or may be variable (e.g., adjusted according to an external temperature detected by a temperature sensor coupled to the oxygen concentrator 100). In some embodiments, the threshold may be set by the user (or, for example, by a doctor's prescription).

At 1805, if the breathing rate is below a first threshold, a subset of the compressors may be used (e.g., one of two compressors may be used). Using a subset of compressors may lower power requirements and conserve the battery. In some embodiments, the user may manually place the oxygen concentrator 100 into a lower power mode that uses a subset of the compressors 301.

At 1807, if the breathing rate is above the first threshold, a greater number than the subset of compressors may be used (e.g., two of two compressors may be used). In some embodiments, if one or more of the available compressors malfunctions, all of the available compressors may be used (regardless of detected breathing rate) until the compressor can be repaired. In some embodiments, fewer than all of the available compressors may be used if another compressor malfunctions.

Figure 19:
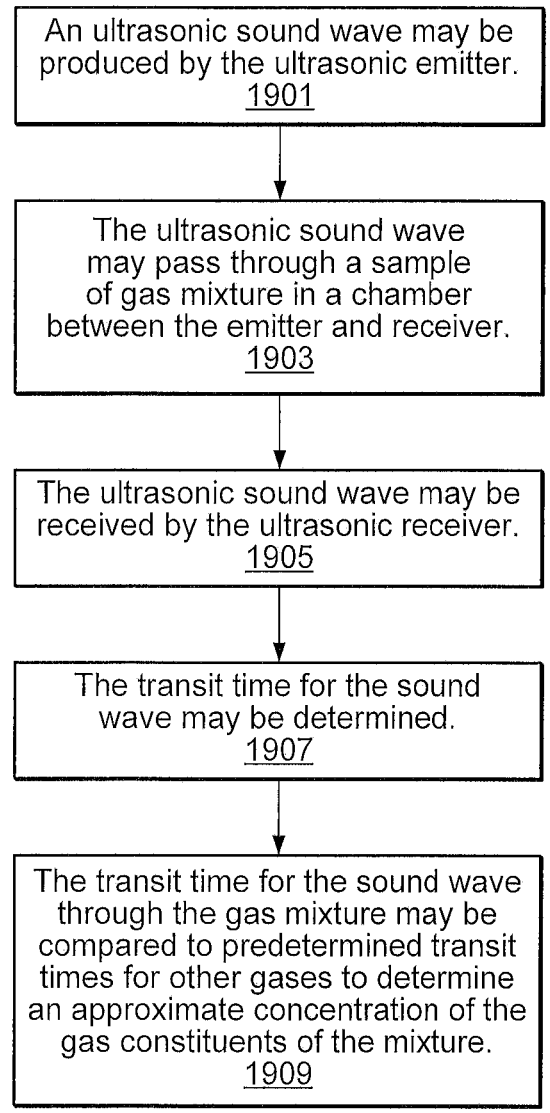
FIG. 19 illustrates a flowchart of an embodiment for ultrasonic sensor operation, according to an embodiment.

FIG. 19 illustrates a flowchart of an embodiment for ultrasonic sensor operation, according to an embodiment. It should be noted that in various embodiments of the methods described below, one or more of the elements described may be performed concurrently, in a different order than shown, or may be omitted entirely. Other additional elements may also be performed as desired.

At 1901, an ultrasonic sound wave may be produced by the ultrasonic emitter 201.

At 1903, the ultrasonic sound wave may pass through a sample of gas mixture (e.g., which may be comprised of mostly oxygen) in a chamber between the emitter 201 and receiver 203.

At 1905, the ultrasonic sound wave may be received by the ultrasonic receiver 203.

At 1907, the transit time for the sound wave may be determined.

At 1909, the transit time for the sound wave through the gas mixture may be compared to predetermined transit times for other gases to determine an approximate concentration of the gas constituents of the mixture. In some embodiments, a phase shift due to structural changes in the housing may be accounted for in the comparison.

Figure 20:
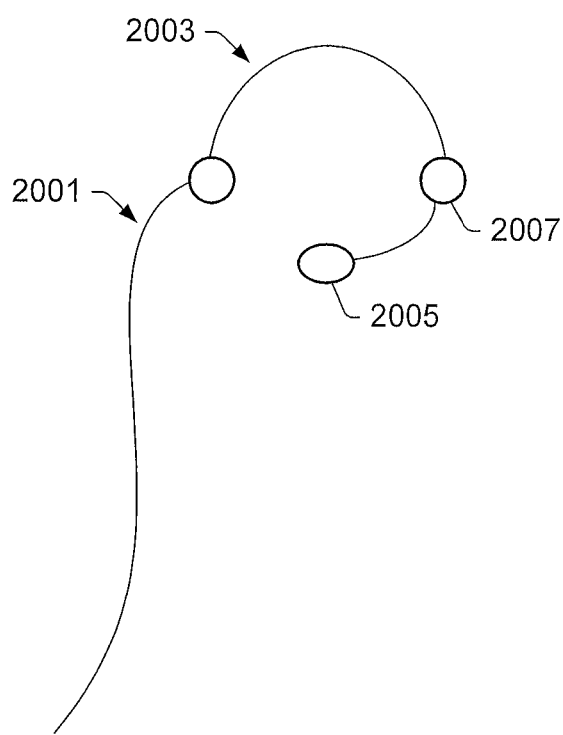
FIG. 20 illustrates a headset/microphone boom, according to an embodiment.

FIG. 20 illustrates an embodiment of a headset/microphone boom 2003. In some embodiments, a device 387 (e.g., an MP3 player, mobile phone, etc.) may be integrated into the oxygen concentrator 100 (e.g., integrated into the outer housing 2101). The microphone 2005 and headphones 2007 may be coupled to the device through a wire 2001 (e.g., which may be coextruded with the tube 909, coupled to wire 905, or wire 2001 and wire 905 may be one wire). The oxygen concentrator may have an audio output/input jack 2109 (other locations of the audio/input jack 2109 are also contemplated). In some embodiments, the headset 2003 may be wireless (e.g., may use Bluetooth™). In some embodiments, the microphone 2005 may be coupled to the nasal cannula 903 and the headphones 2007 may be coupled to wire 905. Other configurations are also contemplated. For example, the oxygen from the oxygen concentrator may be directed at the user's nose and/or mouth from a tube coupled to microphone 2005 (instead of or in addition to a nasal cannula). The microphone 2005 may be embedded in the tube directing the oxygen toward the user's nose and/or mouth (and, correspondingly, may be near the user's mouth). The headset/microphone boom 2003 may also be used with the oxygen concentrator 100 for hands-free cellular phone use. Other uses are also contemplated.

Figure 21B:
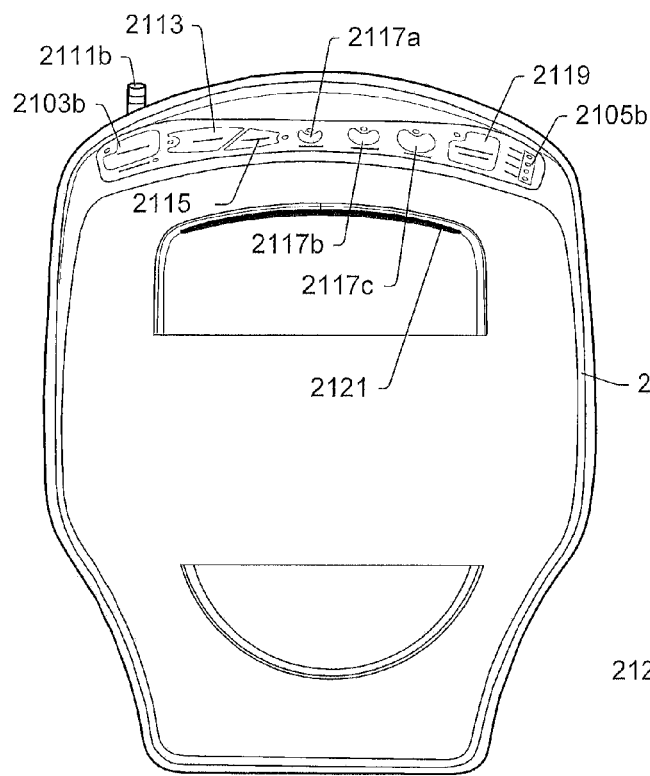
Figure 21C:
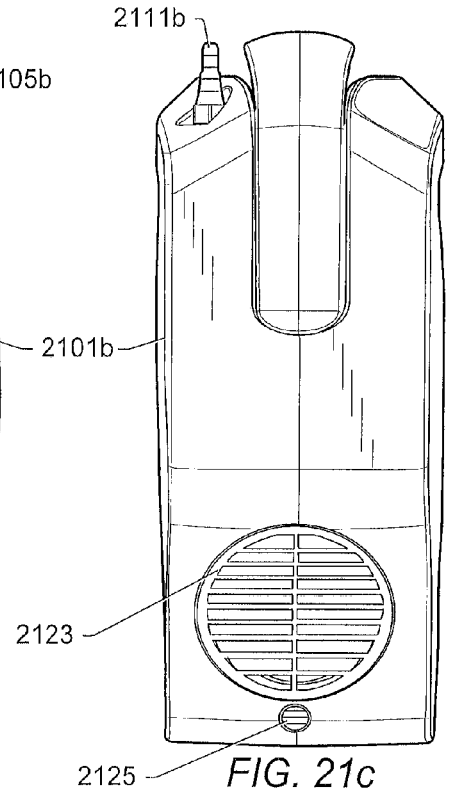
Figure 28A:
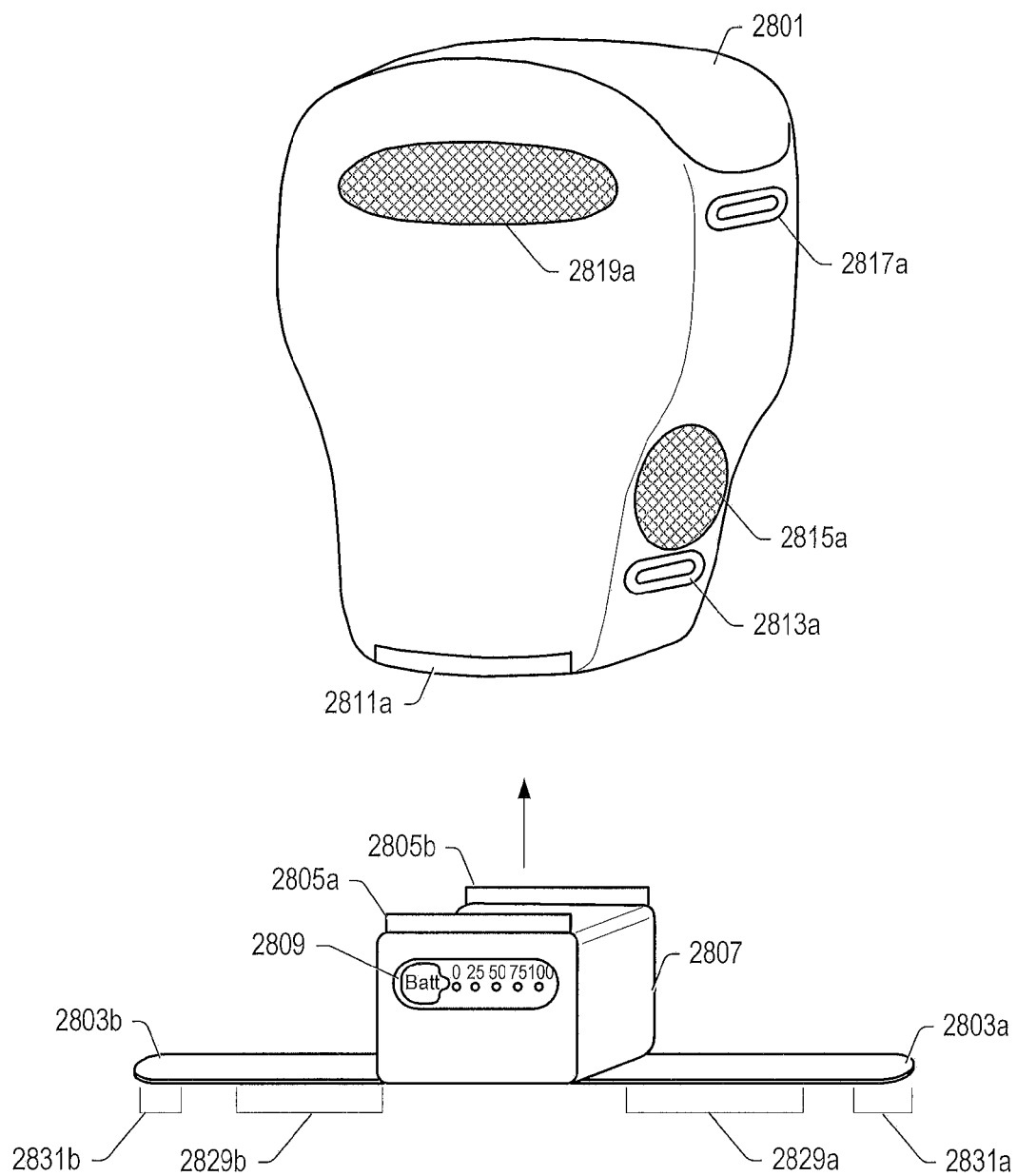
FIGS. 28a-d illustrate an attachable external battery pack for the oxygen concentrator, according to an embodiment.
Figure 28B:
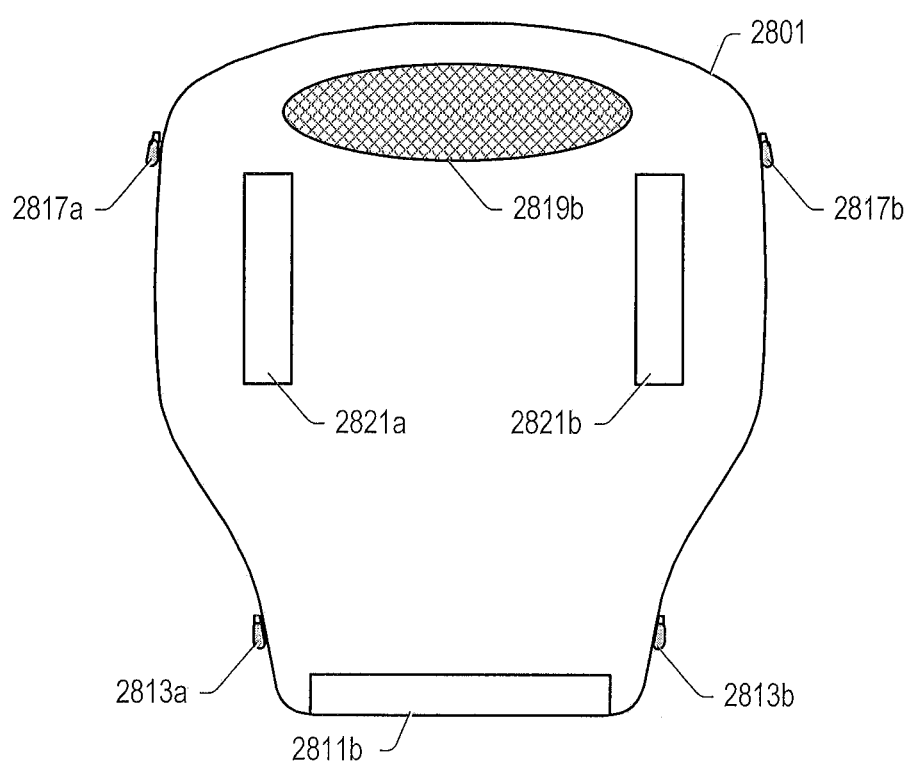
Figure 28C:
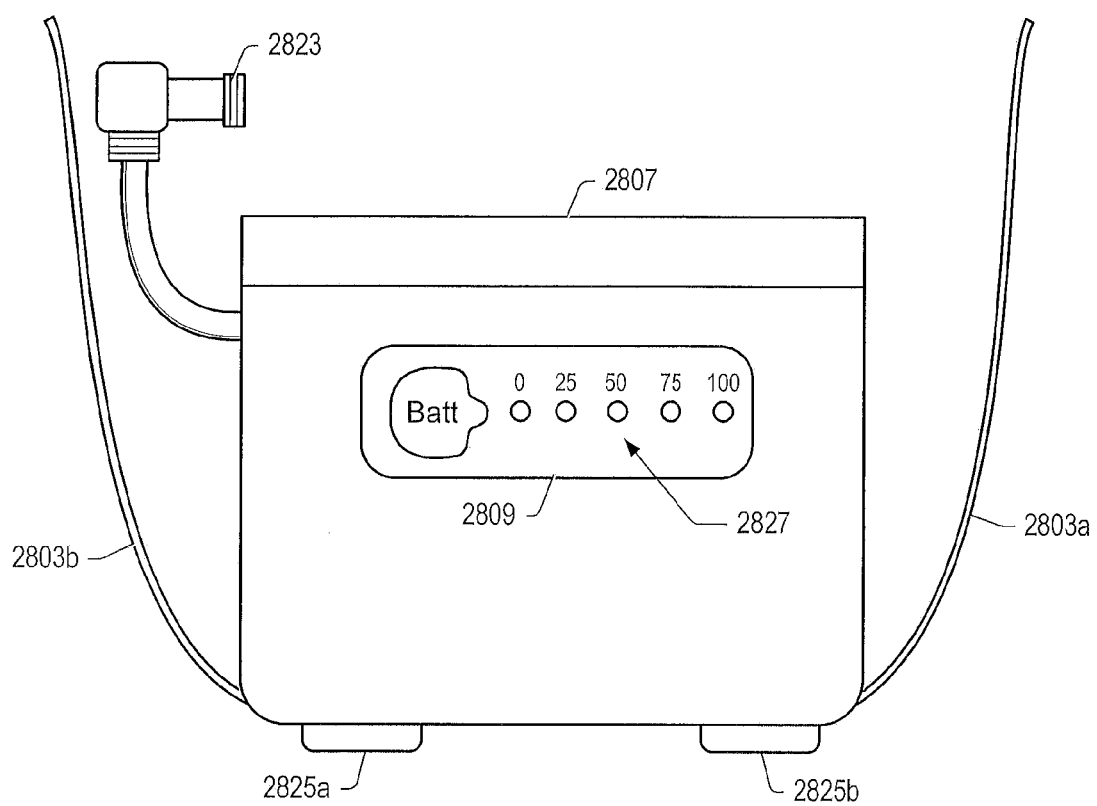
Figure 28D:
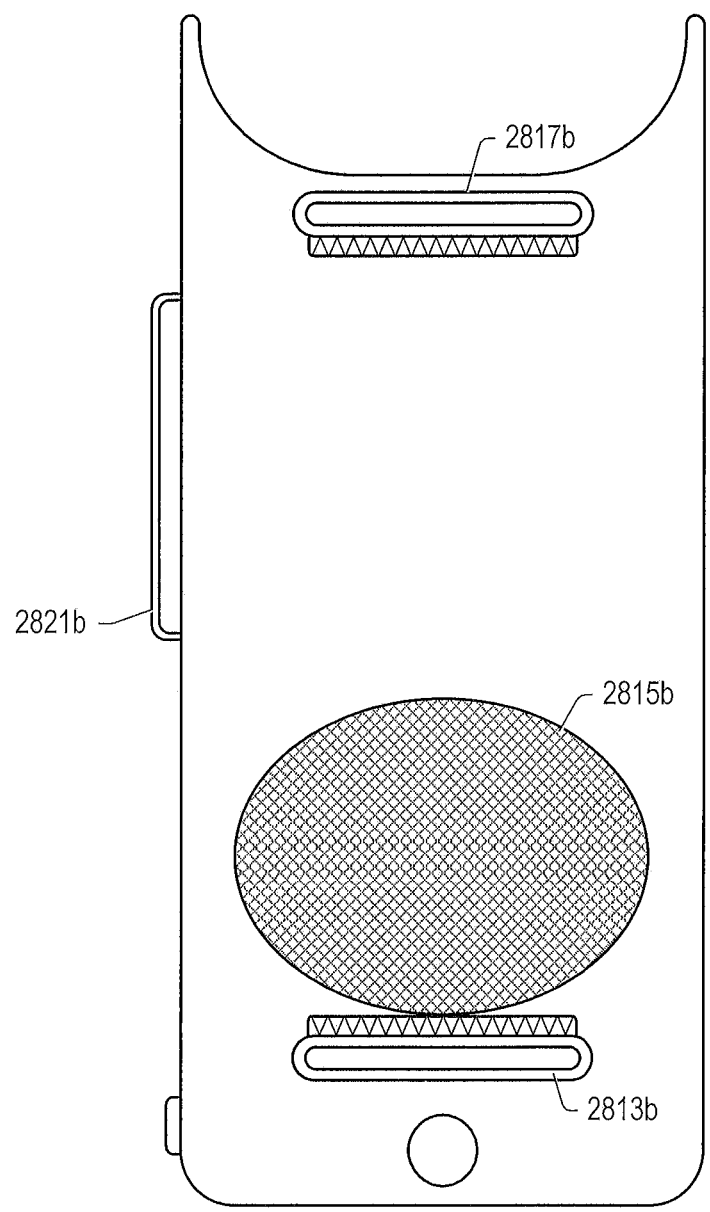

FIGS. 21*a-c* illustrate two embodiments of an outer housing 2101*a,b*. In some embodiments, the outer housing 2101*a,b* may be comprised of a light-weight plastic. Other materials are also contemplated. Other outer housing configurations are also contemplated. In some embodiments, outer housing 2101*b* may include buttons to activate active mode 2113, sleep mode 2115, dosage buttons (e.g., 1 LPM button 2117*a*, 2 LPM button 2117*b*, and 3 LPM button 2117*c*), and a battery check button 2119 (which may result in a relative battery power remaining LED being illuminated in LED panel 2105*b*). In some embodiments, one or more of the buttons may have a respective LED that may illuminate when the respective button is pressed (and may power off when the respective button is pressed again). Other buttons and indicators are also contemplated. In some embodiments, outer housing 2101*b* may include inlet air slot 2121 for receiving external air. Vent 2123 may be used to vent air (e.g., nitrogen) from the oxygen concentrator. In some embodiments, a vent 2123 may also be on the opposing side of the outer housing 2101*b*. Plug receptacle 2125 may plug into an external power adapter or battery pack (e.g., receive connector 2823 as seen in FIG. 28*c*). Other power sources are also contemplated. In some embodiments, the solar panel 1501 may be coupled to an outside of the outer housing 2101*a,b*. In some embodiments, the solar panel 1501 may be coupled to an exterior of a backpack that receives the oxygen concentrator.

Figure 22:
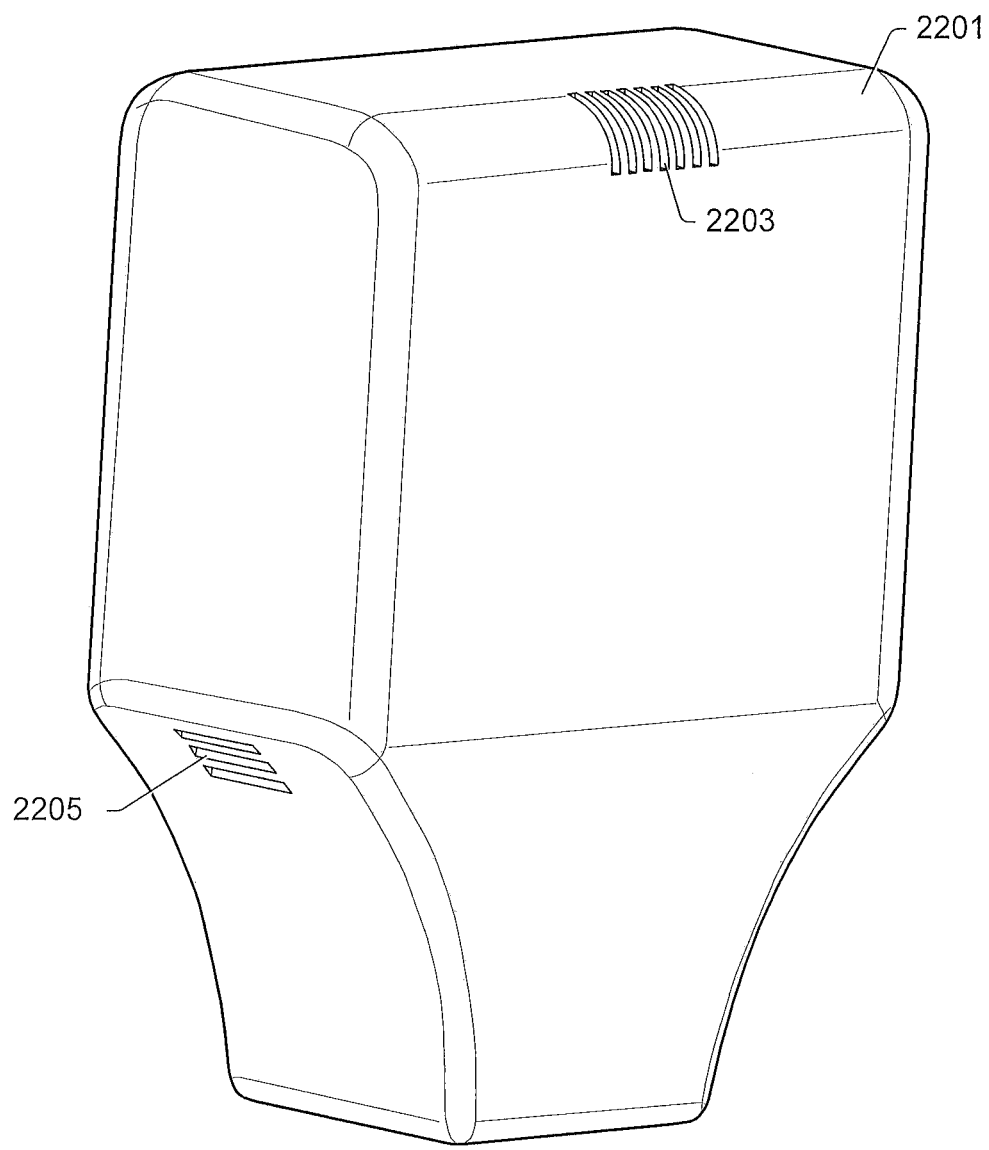
FIG. 22 illustrates an embodiment of an enclosure housing.
Figure 23:
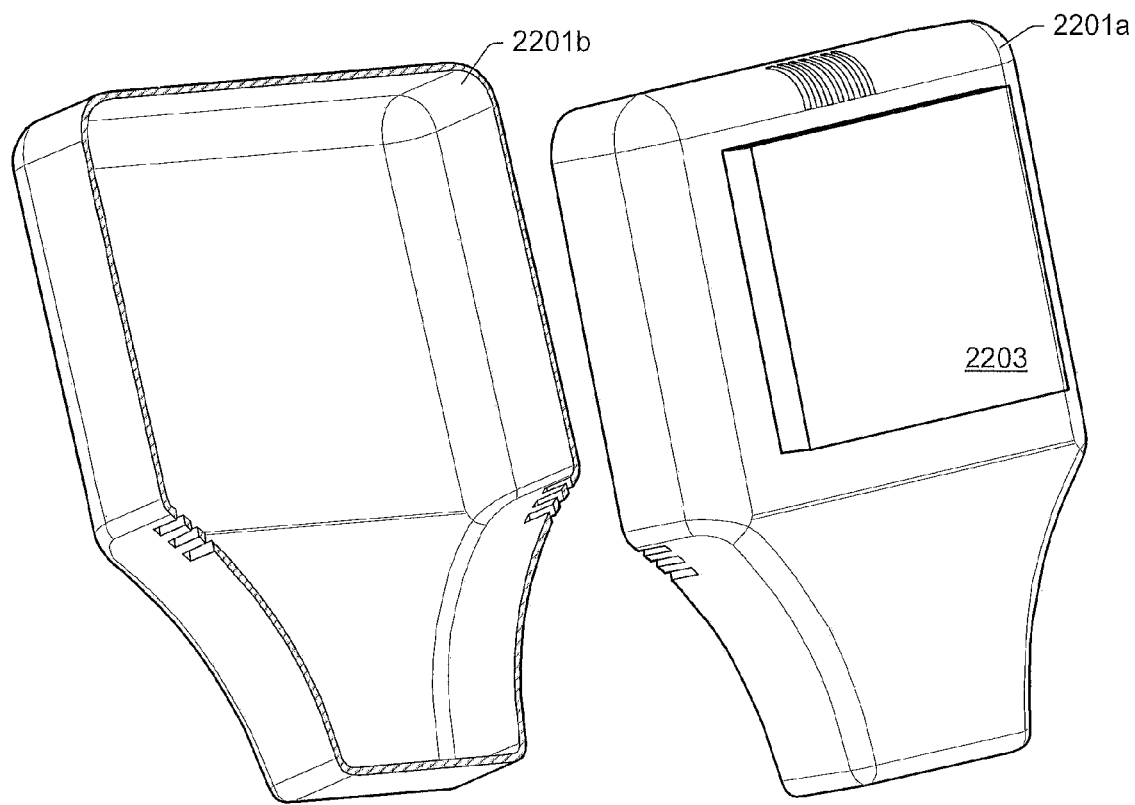
FIG. 23 illustrates an embodiment of two half sections of the enclosure housing.
Figure 24:
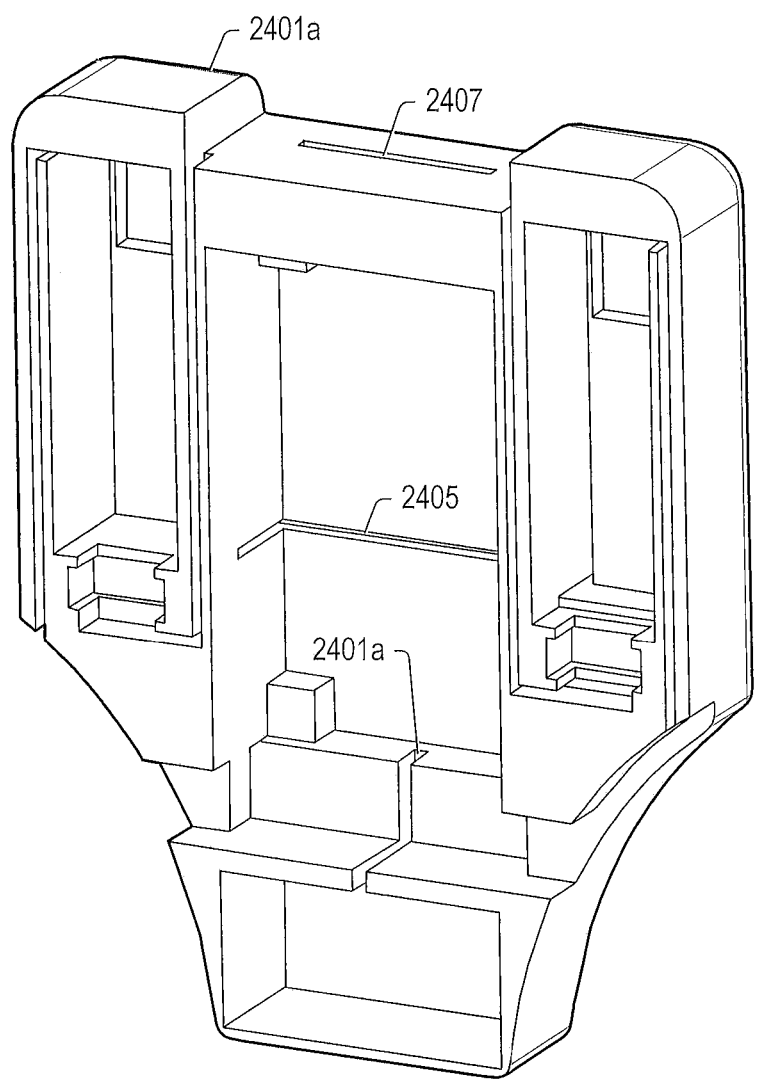
FIG. 24 illustrates an embodiment of a first foam housing.
Figure 25:
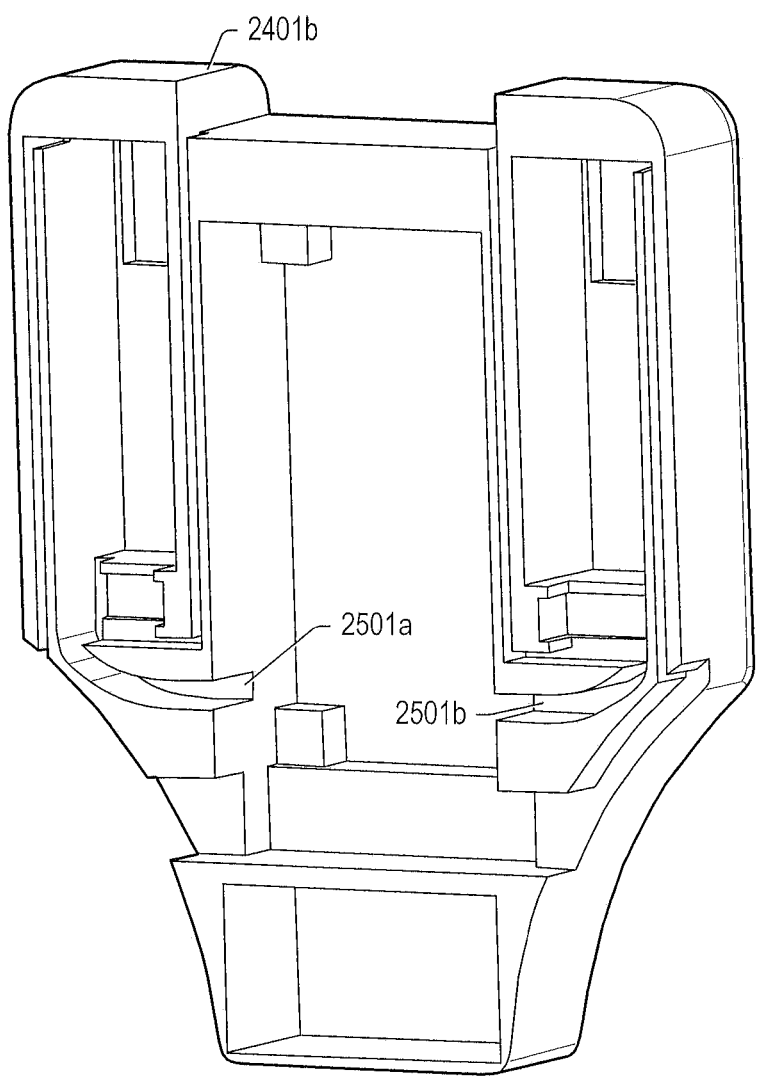
FIG. 25 illustrates an embodiment of a complimentary second foam housing.

FIG. 22 illustrates an embodiment of an enclosure housing 2201. FIG. 23 illustrates an embodiment of two half sections 2201*a,b* of the enclosure housing 2201. In some embodiments, a section of foam 2203 may be included between the enclosure housing 2201 and the outer housing 2101. For example, the foam may be approximately ¼ inch thick. Other thicknesses are also contemplated. The foam may reduce vibration transferred to the outer housing 2101 and/or user. The reduction in vibration may reduce noise (e.g., reduce noise by 1 decibel) from the oxygen concentrator while operating. Other sound reduction levels are also contemplated. In some embodiments, the foam may substantially surround the enclosure housing 2201. In some embodiments, the components of the oxygen concentrator 100 may be placed inside of foam housings (e.g., FIG. 24 illustrates an embodiment of a first foam housing 2401*a* and FIG. 25 illustrates an embodiment of a complimentary second foam housing 2401*b*) and the foam housings 2401 may be placed inside the enclosure housing half sections 2201*a,b*. The enclosure housing half sections 2201*a,b* may be coupled together (e.g., through an adhesive, solvent weld, rivets, etc.) to form enclosure housing 2201. The enclosure housing 2201 may be made of a light-weight plastic. Other materials are also contemplated. The enclosure housing 2201 may then be placed in the outer housing 2101. The foam housings 2401 may be comprised of open cell foam or closed cell foam (which may reduce more internal sound). Other materials for the foam housings 2401 are also contemplated. In some embodiments, the foam housings 2401*a,b* may be separately coupled together (e.g., sealed together through an adhesive or solvent weld). In some embodiments, the oxygen concentrator components may not be rigidly mounted to the enclosure housing 2201, but may be held by the foam (which may also protect the components, for example, from outer forces on the oxygen concentrator). The placement of the oxygen concentrator components in the foam may be aligned for efficiency to reduce the size and weight of the oxygen concentrator.

FIG. 26 illustrates a side and front profile of a component arrangement in the foam housings 2401, according to an embodiment. The foam housings 2401 may be configured to conform to the oxygen concentrator components (e.g., compressors 301a,b, housing components 111a,b, batteries 395a,b, fans 2601a,b, etc.). For example, the foam housings 2401 may be configured with pockets to receive the oxygen concentrator components. The foam housings 2401 may also incorporate airflow passages 2603a-d (e.g., cutouts in the foam). Air may be pulled into (e.g., through vent 2203) and/or moved around in the foam housings 2401 through fans 2601a,b. In some embodiments, vent 2203 may comprise a sonic baffle with a felt air filter. Other air filters are also contemplated. Air entering the vent 2203 may be filtered by the felt prior to entering the compressors 301. Air may move through air pathways/channels in the foam. The channeled foam may reduce/baffle the sound of the air movement. In some embodiments, the expansion and contraction of the sound (e.g., as the sound/air passes through vent 2203) may reduce the sound. The fans 2601 may be, for example, 12 volt, 1-inch square fans. Other types, numbers, and placements of fans may also be used. Warm air and/or nitrogen may exit the enclosure housing 2201 through vent 2205, 2605 and through outer housing 2101 through a corresponding vent (e.g., vent 2107).

In some embodiments, two compressors 301a,b may be used (e.g., two dual-pump diaphragm compressors). In some embodiments, the two compressors 301a,b may be 12 volt compressors. In some embodiments, each compressor may be attached to a fan 2601 (e.g., compressor 301a may be electrically coupled to fan 2601a and compressor 301b may be electrically coupled to fan 2601b). In some embodiments, increasing or decreasing power to a compressor (e.g., compressor 301a) may result in a corresponding increase or decrease in power to the compressor's corresponding fan (e.g., fan 2601a). This may further conserve power by decreasing power to a fan when the fan's corresponding compressor is operating under decreased power (and vice-versa). Other compressor/fan arrangements are also contemplated.

In some embodiments, the airflow passages 2603a-d may be used to for entering cooling air, exiting warm air, nitrogen, etc. In some embodiments, the foam housings 2401 may dampen sound and insulate heat from the oxygen concentrator components (e.g., to prevent hot spots on the outer casings from the oxygen concentrator components). Other configurations of the foam housings 2401 are also contemplated. For example, foam may be applied around the oxygen concentrator components and allowed to set. In some embodiments, materials other then foam may be used.

In some embodiments, passages in the foam housings 2401 may be used for electrical connections. For example, passage 2403 may be used for connections (e.g., wires) from the batteries 395 to various components of the oxygen concentrator (e.g., compressors 301, circuit board 2607, etc.). Passages 2405 and 2407 may also be used for electrical connections. Passages may also be provided for air tubes. For example, passages 2501a and 2501b may be provided for air tubes between the compressors 301 and the housing component 111a. In some embodiments, the oxygen may exit through a tube through passage 2407 and through exit port or exit nozzle 2111a,b in the outer casing (other exit locations are also contemplated).

FIGS. 28a-d illustrate an attachable external battery pack 2807 for the oxygen concentrator, according to an embodiment. In some embodiments, an outer covering 2801 on the oxygen concentrator may include various fasteners for coupling the oxygen concentrator to external battery pack 2807. For example, Velcro™ receiving portions 2811a,b may receive Velcro™ tabs 2805a,b, respectively. For example, Velcro™ receiving portions 2811a,b may include Velcro™ loops and tabs 2805a,b may include Velcro™ hooks. Other configurations are also contemplated. In some embodiments, straps 2803a,b may loop through receiving rings 2813a,b, respectively. The straps 2803a,b may be pulled through their respective rings 2813a,b, and then the strap may be folded over (with the fold aligned with the rings 2813a,b). Straps 2803a,b may also have Velcro™ portions. For example, Velcro™ portions 2831a,b (e.g., hook portions) may engage respective Velcro™ portions 2829a,b (e.g., loop portions) when the straps 2803a,b are folded over (after passage through their respective hooks 2813a,b). Other Velcro™ placements are also contemplated (e.g., between a top of external battery pack 2807 and the bottom of cover 2801). Other fastener types are also contemplated (e.g., adhesive, tape, buckles, etc). In some embodiments, the covering 2801 may include one or more mesh vents (e.g., vents 2819a,b, and 2815a,b). Covering 2801 may also include belt loops 2821a,b to receive a user belt (e.g., to hold the oxygen concentrator on a user's waist). Rings 2817a,b may be used to attach a shoulder strap to carry the oxygen concentrator over a user's shoulder (e.g., a strap with respective Velcro™ portions may be inserted through each ring and the Velcro™ portions folded over on each other). In some embodiments, the external battery pack 2807 may include a connector 2823 to plug into a receiving connector (e.g., plug receptacle 2125 in FIG. 21c) on the oxygen concentrator to deliver power from the batteries in the external battery pack 2807. The external battery pack 2807 may include, for example, 16 cells to deliver direct current (other battery types and cell numbers are also contemplated). The battery pack 2807 may also include a battery power indicator 2809. For example, a series of light emitting diodes (LEDs) 2827 may light up to indicate an amount of battery power remaining (e.g., 0%, 25%, 50%, 75%, 100%, etc). Other indicators are also contemplated. In some embodiments, the external battery pack 2807 may include feet 2825a,b. In some embodiments, the covering 2801 may be made of canvas, nylon, plastic, etc. Other materials for the covering are also contemplated. In some embodiments, rings 2813a,b and 2817a,b may be made of stainless steel, plastic, etc. Rings 2813a,b and 2817a,b may be fastened to the covering 2801 through adhesive, through sewed-on patches (e.g., which overlap a portion of the respective ring), etc. Feet 2825a,b may be made of rubber (other materials for the feet 2825a,b are also contemplated).

Embodiments of a subset or all (and portions or all) of the above may be implemented by program instructions stored in a memory medium (e.g., memory 397) or carrier medium and executed by a processor (e.g., processor 399). A memory medium may include any of various types of memory devices or storage devices. The term "memory medium" is intended to include an installation medium, e.g., a Compact Disc Read Only Memory (CD-ROM), floppy disks, or tape device; a computer system memory or random access memory such as Dynamic Random Access Memory (DRAM), Double Data Rate Random Access Memory (DDR RAM), Static Random Access Memory (SRAM), Extended Data Out Random Access Memory (EDO RAM), Rambus Random Access Memory (RAM), etc.; or a non-volatile memory such as a magnetic media, e.g., a hard drive, or optical storage. The memory medium may comprise other types of memory as well, or combinations thereof. In addition, the memory medium may be located in a first computer in which the programs are executed, or may be located in a second different computer that connects to the first computer over a network, such as the Internet. In the latter instance, the second computer may provide program instructions to the first computer for execution. The term "memory medium" may include two or more memory mediums that may reside in different locations, e.g., in different computers that are connected over a network.

In some embodiments, a computer system at a respective participant location may include a memory medium(s) on which one or more computer programs or software components according to one embodiment of the present invention may be stored. For example, the memory medium may store one or more programs that are executable to perform the methods described herein. The memory medium may also store operating system software, as well as other software for operation of the computer system.

Further modifications and alternative embodiments of various aspects of the invention may be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

We claim:

1. An oxygen concentrator apparatus, comprising:
at least two canisters, wherein a first canister and a second canister are integrated into a molded housing;
separation material disposed in at least the first canister and the second canister, wherein the separation material separates at least some nitrogen from air in the canister to produce oxygen enriched gas;
a compression system coupled to at least one canister, wherein the compression system compresses air during operation; and
a chamber coupled to one or more of the canisters, wherein oxygen enriched gas produced in one or more of the canisters is passed into the chamber during use;
an ultrasonic emitter operable to provide an ultrasonic sound wave through the chamber;
an ultrasonic receiver for detecting the ultrasonic sound wave that has traveled through the chamber, wherein the ultrasonic emitter and the ultrasonic receiver are coupled to the chamber, and wherein the ultrasonic emitter and the ultrasonic receiver are positioned on opposing sides of the chamber, in alignment with each other;
an inlet conduit and an outlet conduit coupled to the chamber, wherein the inlet conduit and the outlet conduit are positioned on opposing walls of the chamber, and
wherein oxygen enriched gas enters the chamber through the inlet conduit and exits the chamber through the outlet conduit such that the oxygen enriched gas passes through the opposing walls of the chamber perpendicular to an axial axis formed between the ultrasonic emitter and the ultrasonic receiver; and
a processor coupled to the ultrasonic emitter and the ultrasonic receiver, wherein the processor is operable to execute program instructions, and wherein the program instructions are operable to assess a concentration of oxygen in the chamber based on the speed of ultrasonic sound waves produced by the ultrasonic emitter and received by the ultrasonic receiver;
wherein the program instructions are further operable to:
measure a first phase shift of the ultrasonic sound wave between the ultrasonic emitter and the ultrasonic receiver;
measure a second phase shift of the ultrasonic sound wave between the ultrasonic emitter and the ultrasonic receiver at a later time than the first phase shift;
use a difference between the first phase shift and the second phase shift to determine the relative concentration of the constituent of the gas.

2. The apparatus of claim 1, wherein a distance between the ultrasonic emitter and the ultrasonic receiver is greater than at least two times a wavelength of the ultrasonic sound wave.

3. The apparatus of claim 1, further comprising:
one or more conduits coupled to one or more canisters;
an airway delivery device coupled to one or more of conduits and positionable on the face of a user;
a pressure sensor coupled to the airway delivery device; wherein the pressure sensor is operable to detect a change in pressure at the airway delivery device; and
wherein the program instructions are further operable to direct oxygen enriched gas from one or more of the canisters through one or more of the conduits to the airway delivery device in response to detecting a drop in pressure at the airway delivery device.

4. The apparatus of claim 3, further comprising a valve positioned between one or more of the conduits and the airway delivery device, wherein the valve controls release of oxygen enriched gas from one or more of the canisters such that a pulse of oxygen enriched gas passes through the airway delivery device.

5. The apparatus of claim 3, wherein the program instructions are further operable to control the operation of the valve to deliver a bolus of oxygen enriched gas to a user in two or more pulses; wherein a total volume of the bolus is approximately an amount of oxygen determined to be delivered to the user during a single breath.

6. The apparatus of claim 1, comprising:
wherein the at least two canisters comprise a first canister containing separation material and a second canister containing separation material;
the apparatus further comprising one or more conduits coupling the first canister to the second canister;
wherein one or more of the conduits couple the first canister to the second canister such that at least part of oxygen enriched gas from the first canister is diverted through the second canister during at least part of a venting process of the second canister; and
wherein one or more of the conduits couple the first canister to the second canister such that at least part of oxygen enriched gas from the second canister is diverted through the first canister during at least part of a venting process of the first canister.

7. The apparatus of claim 1, wherein the separation material comprises a zeolite.

8. A method of providing oxygen enriched gas to a user of an oxygen concentrator, the oxygen concentrator comprising:
at least two canisters wherein a first canister and a second canister are integrated into a molded housing;
separation material disposed in at least the first canister and the second canister, wherein the separation material separates at least some nitrogen from air in the canister to produce oxygen enriched gas;

a compression system coupled to at least one canister, wherein the compression system compresses air during operation; and a chamber coupled to one or more of the canisters, wherein oxygen enriched gas produced in one or more of the canisters is passed into the chamber during use;

an ultrasonic emitter operable to provide an ultrasonic sound wave through the chamber; and an ultrasonic receiver for detecting the ultrasonic sound wave that has traveled through the chamber, wherein the ultrasonic emitter and the ultrasonic receiver are positioned on opposing sides of the chamber, in alignment with each other;

an inlet conduit and an outlet conduit coupled to the chamber, wherein the inlet conduit and the outlet conduit are positioned on opposing walls of the chamber, and wherein oxygen enriched gas enters the chamber through the inlet conduit and exits the chamber through the outlet conduit such that the oxygen enriched gas passes through the opposing walls of the chamber perpendicular to an axial axis formed between the ultrasonic emitter and the ultrasonic receiver;

the method comprising:

operating the compression system to compress air during operation of a motor;

passing the compressed air into one or more of the canisters, wherein oxygen is at least partially separated from air in one or more of the canisters to produce oxygen enriched gas;

passing the produced oxygen enriched gas from one or more canisters to the chamber;

transmitting an ultrasonic sound wave through the oxygen enriched gas in the chamber, wherein the ultrasonic sound wave is provided by the ultrasonic emitter;

receiving the ultrasonic sound wave at the ultrasonic receiver;

measuring a first phase shift of the sound wave between the ultrasonic emitter and the ultrasonic receiver;

measuring a second phase shift of the sound wave between the ultrasonic emitter and the ultrasonic receiver at a later time than the first phase shift;

using a difference between the first phase shift and the second phase shift to assess the relative concentration of the constituent of the gas; and directing the oxygen enriched gas from the chamber to the user.

9. The method of claim 8, wherein a distance between the ultrasonic emitter and the ultrasonic receiver is greater than at least two times a wavelength of the ultrasonic sound wave.

10. The method of claim 8, wherein the oxygen concentrator further comprises:

an airway delivery device coupled to one or more canisters and positionable on the face of a user; and a pressure sensor coupled to the airway delivery device; wherein the pressure sensor is operable to detect a change in pressure at the airway delivery device;

wherein the method further comprises:

directing the oxygen enriched gas to the airway delivery device in response to detecting a drop in pressure at the airway delivery device.

11. The method of claim 10, further comprising:

assessing a change in pressure during an inhalation of the user;

assessing a pressure change rate based on the detected user inhalation; and if the pressure change rate indicates the user is in an active state, implement a first mode of providing oxygen enriched gas to the user; and if the pressure change rate indicates the oxygen concentrator user is in a sedentary state, implement a second mode of delivery of oxygen enriched gas to the user, the second mode of delivery being different from the first mode of delivery.

12. The method of claim 8, wherein directing the oxygen enriched gas to the user comprises providing a pulse of the oxygen enriched gas to an airway delivery device coupled to the user's face.

13. The method of claim 8, wherein directing the oxygen enriched gas to the user comprises delivering a bolus of oxygen enriched gas to a user in two or more pulses, wherein a volume of the bolus is approximately an amount of oxygen determined to be delivered to the user during a single breath.

14. The method of claim 8, wherein the at least two canisters comprise a first canister containing separation material and a second canister containing separation material;

wherein the apparatus further comprises one or more conduits coupling the first canister to the second canister;

wherein the method further comprises:

venting nitrogen gas from the second canister;

diverting at least a portion of oxygen enriched gas produced in the first canister through the second canister during the venting of the second canister;

venting nitrogen gas from the first canister;

diverting at least a portion of oxygen enriched gas produced in the second canister through the first canister during the venting of the second canister.

15. The method of claim 8, wherein the separation material comprises a zeolite.

* * * * *